(12) United States Patent
Tsougarakis et al.

(10) Patent No.: US 8,965,088 B2
(45) Date of Patent: *Feb. 24, 2015

(54) METHODS FOR DETERMINING MENISCAL SIZE AND SHAPE AND FOR DEVISING TREATMENT

(71) Applicant: ConforMIS, Inc., Bedford, MA (US)

(72) Inventors: Konstantinos Tsougarakis, San Francisco, CA (US); Daniel Steines, Lexington, MA (US); Bhaskar Rao Vissa, San Jose, CA (US); Philipp Lang, Lexington, MA (US); Barry J. Linder, Danville, CA (US)

(73) Assignee: ConforMIS, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,707

(22) Filed: Jan. 17, 2014

(65) Prior Publication Data

US 2014/0153798 A1 Jun. 5, 2014

Related U.S. Application Data

(63) Continuation of application No. 13/312,339, filed on Dec. 6, 2011, now Pat. No. 8,634,617, which is a continuation of application No. 12/853,599, filed on Aug. 10, 2010, now Pat. No. 8,077,950, which is a (Continued)

(51) Int. Cl.
*G06K 9/00* (2006.01)
*G06T 7/00* (2006.01)

(Continued)

(52) U.S. Cl.
CPC ........... *G06T 7/0012* (2013.01); *A61F 2/30756* (2013.01); *A61F 2/30942* (2013.01);

(Continued)

(58) Field of Classification Search
CPC .................................. G06K 9/00; A61B 1/00
USPC ......... 382/128–134; 378/65, 68, 69; 600/407, 600/435, 437, 439; 424/422, 423, 424, 425, 424/426; 324/309; 128/915, 916
See application file for complete search history.

(56) References Cited

U.S. PATENT DOCUMENTS

| 3,314,420 A | 4/1967 | Smith et al. ..................... 128/92 |
| 3,605,123 A | 9/1971 | Hahn .................................. 3/1 |

(Continued)

FOREIGN PATENT DOCUMENTS

| CN | 86209787 | 11/1987 | ................ A61F 2/38 |
| CN | 2305966 | 2/1999 | ................ A61F 2/28 |

(Continued)

OTHER PUBLICATIONS

United States Patent and Trademark Office, Office Action dated Feb. 3, 2011, pertaining to U.S. Appl. No. 12/614,946, 15 pages.

(Continued)

*Primary Examiner* — Abolfazl Tabatabai
(74) *Attorney, Agent, or Firm* — Sunstein Kann Murphy & Timbers LLP

(57) ABSTRACT

The present invention relates to methods for determining meniscal size and shape for use in designing therapies for the treatment of various joint diseases. The invention uses an image of a joint that is processed for analysis. Analysis can include, for example, generating a thickness map, a cartilage curve, or a point cloud. This information is used to determine the extent of the cartilage defect or damage and to design an appropriate therapy, including, for example, an implant. Adjustments to the designed therapy are made to account for the materials used.

19 Claims, 10 Drawing Sheets

Related U.S. Application Data continuation of application No. 10/704,325, filed on Nov. 7, 2003, now Pat. No. 7,796,791.

(60) Provisional application No. 60/424,964, filed on Nov. 7, 2002.

(51) Int. Cl.

| | | |
|---|---|---|
| *A61F 2/30* | (2006.01) | |
| *A61B 17/58* | (2006.01) | |
| *A61B 5/107* | (2006.01) | |
| *A61B 5/00* | (2006.01) | |
| *A61F 2/32* | (2006.01) | |
| *A61F 2/34* | (2006.01) | |
| *A61F 2/36* | (2006.01) | |
| *A61F 2/38* | (2006.01) | |
| *A61F 2/40* | (2006.01) | |
| *A61F 2/42* | (2006.01) | |
| *A61F 2/44* | (2006.01) | |

(52) U.S. Cl.
CPC ............ *A61B5/1075* (2013.01); *A61B 5/4514* (2013.01); *A61B 5/4528* (2013.01); *A61F 2/32* (2013.01); *A61F 2/34* (2013.01); *A61F 2/36* (2013.01); *A61F 2/38* (2013.01); *A61F 2/3804* (2013.01); *A61F 2/40* (2013.01); *A61F 2/4202* (2013.01); *A61F 2/4241* (2013.01); *A61F 2/4261* (2013.01); *A61F 2/44* (2013.01); *A61F 2002/30133* (2013.01); *A61F 2002/30894* (2013.01); *A61F 2002/30943* (2013.01); *A61F 2002/30948* (2013.01); *A61F 2002/30952* (2013.01); *A61F 2230/0015* (2013.01)
USPC ............................................. 382/128; 606/88

(56) References Cited

U.S. PATENT DOCUMENTS

| | | | |
|---|---|---|---|
| 3,694,820 A | 10/1972 | Scales et al. ................. 3/1 |
| 3,798,679 A | 3/1974 | Ewald ......................... 3/1 |
| 3,808,606 A | 5/1974 | Tronzo ........................ 3/1 |
| 3,816,855 A | 6/1974 | Saleh .......................... 3/1 |
| 3,843,975 A | 10/1974 | Tronzo ........................ 3/1 |
| 3,852,830 A | 12/1974 | Marmor ....................... 3/1 |
| 3,855,638 A | 12/1974 | Pilliar ......................... 3/1 |
| 3,938,198 A | 2/1976 | Kahn et al. ............... 3/1.912 |
| 3,987,499 A | 10/1976 | Scharbach et al. ............ 3/1.91 |
| 3,991,425 A | 11/1976 | Martin et al. ............... 3/1.91 |
| 4,052,753 A | 10/1977 | Dedo .......................... 3/1 |
| 4,055,862 A | 11/1977 | Farling ..................... 3/1.91 |
| 4,085,466 A | 4/1978 | Goodfellow et al. ......... 3/1.91 |
| 4,098,626 A | 7/1978 | Graham et al. ............. 149/19.4 |
| 4,164,793 A | 8/1979 | Swanson .................... 3/1.91 |
| 4,178,641 A | 12/1979 | Grundei et al. ............. 3/1.911 |
| 4,203,444 A | 5/1980 | Bonnell et al. .............. 128/276 |
| 4,207,627 A | 6/1980 | Cloutier .................... 3/1.911 |
| 4,211,228 A | 7/1980 | Cloutier .................... 128/303 R |
| 4,213,816 A | 7/1980 | Morris ...................... 156/245 |
| 4,219,893 A | 9/1980 | Noiles ...................... 3/1.911 |
| 4,280,231 A | 7/1981 | Swanson .................... 3/1.91 |
| 4,309,778 A | 1/1982 | Buechel et al. ............. 3/1.911 |
| 4,340,978 A | 7/1982 | Buechel et al. ............. 3/1.911 |
| 4,344,193 A | 8/1982 | Kenny ...................... 3/1.911 |
| 4,368,040 A | 1/1983 | Weissman .................. 433/36 |
| 4,436,684 A | 3/1984 | White ....................... 264/138 |
| 4,459,985 A | 7/1984 | McKay et al. .............. 128/303 R |
| 4,502,161 A | 3/1985 | Wall ......................... 3/1.91 |
| 4,575,805 A | 3/1986 | Moermann et al. ........... 364/474 |
| 4,586,496 A | 5/1986 | Keller ....................... 128/92 E |
| 4,594,380 A | 6/1986 | Chapin et al. ............... 524/144 |
| 4,601,290 A | 7/1986 | Effron et al. ................ 128/305 |
| 4,609,551 A | 9/1986 | Caplan et al. ............... 424/95 |
| 4,627,853 A | 12/1986 | Campbell et al. ............. 623/16 |
| 4,655,227 A | 4/1987 | Gracovetsky ................ 128/781 |
| 4,662,889 A | 5/1987 | Zichner et al. ................ 623/20 |
| 4,699,156 A | 10/1987 | Gracovetsky ................ 128/781 |
| 4,714,472 A | 12/1987 | Averill et al. ................. 623/20 |
| 4,714,474 A | 12/1987 | Brooks, Jr. et al. ............ 623/20 |
| 4,769,040 A | 9/1988 | Wevers ........................ 623/20 |
| 4,813,436 A | 3/1989 | Au ............................ 128/779 |
| 4,822,365 A | 4/1989 | Walker et al. ................. 623/20 |
| 4,823,807 A | 4/1989 | Russell et al. ................ 128/773 |
| 4,846,835 A | 7/1989 | Grande ........................ 623/11 |
| 4,865,607 A | 9/1989 | Witzel et al. .................. 623/20 |
| 4,872,452 A | 10/1989 | Alexson ..................... 128/92 VJ |
| 4,880,429 A | 11/1989 | Stone .......................... 623/18 |
| 4,883,488 A | 11/1989 | Bloebaum et al. .................. 3/20 |
| 4,888,021 A | 12/1989 | Forte et al. ................... 623/20 |
| 4,936,853 A | 6/1990 | Fabian et al. ................. 623/20 |
| 4,936,862 A | 6/1990 | Walker et al. ................. 623/23 |
| 4,944,757 A | 7/1990 | Martinez et al. ............... 623/20 |
| 5,019,103 A | 5/1991 | Van Zile et al. ............... 623/20 |
| 5,021,061 A | 6/1991 | Wevers et al. ................. 623/20 |
| 5,041,138 A | 8/1991 | Vacanti et al. ................ 623/16 |
| 5,047,057 A | 9/1991 | Lawes ........................ 623/20 |
| 5,059,216 A | 10/1991 | Winters ....................... 623/20 |
| 5,067,964 A | 11/1991 | Richmond et al. ............. 623/18 |
| 5,099,859 A | 3/1992 | Bell ........................... 128/781 |
| 5,108,452 A | 4/1992 | Fallin ......................... 623/23 |
| 5,123,927 A | 6/1992 | Duncan et al. ................ 623/20 |
| 5,129,908 A | 7/1992 | Peterson ...................... 606/88 |
| 5,133,759 A | 7/1992 | Turner ........................ 623/20 |
| 5,150,304 A | 9/1992 | Berchem et al. ............ 364/474.24 |
| 5,152,797 A | 10/1992 | Luckman et al. ............... 623/20 |
| 5,154,178 A | 10/1992 | Shah ......................... 128/653.2 |
| 5,162,430 A | 11/1992 | Rhee et al. ................... 525/54.1 |
| 5,171,244 A | 12/1992 | Caspari et al. ................. 606/88 |
| 5,171,322 A | 12/1992 | Kenny ........................ 623/18 |
| 5,197,985 A | 3/1993 | Caplan et al. ................. 623/16 |
| 5,206,023 A | 4/1993 | Hunziker ..................... 424/423 |
| 5,226,914 A | 7/1993 | Caplan et al. ................. 623/16 |
| 5,234,433 A | 8/1993 | Bert et al. ..................... 606/88 |
| 5,245,282 A | 9/1993 | Mugler, III et al. ........... 324/309 |
| 5,246,013 A | 9/1993 | Frank et al. .................. 128/774 |
| 5,246,530 A | 9/1993 | Bugle et al. .................. 156/643 |
| 5,270,300 A | 12/1993 | Hunziker ..................... 514/12 |
| 5,274,565 A | 12/1993 | Reuben .................... 364/474.24 |
| 5,282,868 A | 2/1994 | Bahler ........................ 623/20 |
| 5,288,797 A | 2/1994 | Khalil et al. .................. 524/872 |
| 5,303,148 A | 4/1994 | Mattson et al. ............ 364/413.01 |
| 5,306,307 A | 4/1994 | Senter et al. .................. 623/17 |
| 5,306,311 A | 4/1994 | Stone et al. ................... 623/18 |
| 5,314,478 A | 5/1994 | Oka et al. .................... 623/18 |
| 5,314,482 A | 5/1994 | Goodfellow et al. ............ 623/20 |
| 5,320,102 A | 6/1994 | Paul et al. .................. 128/653.2 |
| 5,326,363 A | 7/1994 | Aikins ......................... 623/20 |
| 5,326,365 A | 7/1994 | Alvine ........................ 623/21 |
| 5,344,459 A | 9/1994 | Swartz ........................ 623/18 |
| 5,360,446 A | 11/1994 | Kennedy ...................... 623/16 |
| 5,365,996 A | 11/1994 | Crook ......................... 164/45 |
| 5,368,858 A | 11/1994 | Hunziker ..................... 424/423 |
| 5,403,319 A | 4/1995 | Matsen, III et al. ............. 606/88 |
| 5,405,395 A | 4/1995 | Coates ........................ 623/20 |
| 5,413,116 A | 5/1995 | Radke et al. .................. 128/777 |
| 5,423,828 A | 6/1995 | Benson ....................... 606/102 |
| 5,433,215 A | 7/1995 | Athanasiou et al. ........... 128/774 |
| 5,445,152 A | 8/1995 | Bell et al. ................... 128/653.5 |
| 5,448,489 A | 9/1995 | Reuben .................... 364/474.05 |
| 5,468,787 A | 11/1995 | Braden et al. ................. 523/113 |
| 5,478,739 A | 12/1995 | Slivka et al. ............... 435/240.23 |
| 5,489,309 A | 2/1996 | Lackey et al. ................. 623/19 |
| 5,501,687 A | 3/1996 | Willert et al. .................. 606/94 |
| 5,503,162 A | 4/1996 | Athanasiou et al. ........... 128/774 |
| 5,507,820 A | 4/1996 | Pappas ........................ 623/20 |
| 5,510,121 A | 4/1996 | Rhee et al. ................... 424/520 |
| 5,522,900 A | 6/1996 | Hollister ...................... 623/18 |
| 5,523,843 A | 6/1996 | Yamane et al. ................ 356/363 |
| 5,541,515 A | 7/1996 | Tsujita ........................ 324/318 |
| 5,549,690 A | 8/1996 | Hollister et al. ............... 623/21 |
| 5,554,190 A | 9/1996 | Draenert ...................... 623/16 |
| 5,556,432 A | 9/1996 | Kubein-Meesenburg et al. ................ 623/20 |

(56) References Cited

U.S. PATENT DOCUMENTS

| | | | |
|---|---|---|---|
| 5,560,096 A | 10/1996 | Stephens | 29/558 |
| 5,564,437 A | 10/1996 | Bainville et al. | 128/774 |
| 5,571,191 A | 11/1996 | Fitz | 623/17 |
| 5,571,205 A | 11/1996 | James | 623/24 |
| 5,609,640 A | 3/1997 | Johnson | 623/20 |
| 5,611,802 A | 3/1997 | Samuelson et al. | 606/86 |
| 5,616,146 A | 4/1997 | Murray | 606/80 |
| 5,632,745 A | 5/1997 | Schwartz | 606/75 |
| 5,671,741 A | 9/1997 | Lang et al. | 128/653.2 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/88 |
| 5,759,205 A | 6/1998 | Valentini | 623/16 |
| 5,768,134 A | 6/1998 | Swaelens et al. | 364/468.28 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A | 10/1998 | Sahay et al. | 623/16 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,643 A | 5/1999 | Walker | 623/20 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,968,099 A | 10/1999 | Badorf et al. | 623/20 |
| 5,972,385 A | 10/1999 | Liu et al. | 424/486 |
| 5,995,738 A | 11/1999 | DiGioia, III et al. | 395/500.32 |
| 6,002,859 A | 12/1999 | DiGioia, III et al. | 395/500.32 |
| 6,013,103 A | 1/2000 | Kaufman et al. | 623/20 |
| 6,046,379 A | 4/2000 | Stone et al. | 623/11 |
| 6,057,927 A | 5/2000 | Lévesque et al. | 356/432 T |
| 6,078,680 A | 6/2000 | Yoshida et al. | 382/128 |
| 6,081,577 A | 6/2000 | Webber | 378/23 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,102,955 A | 8/2000 | Mendes et al. | 623/20 |
| 6,110,209 A | 8/2000 | Stone | 623/16.11 |
| 6,112,109 A | 8/2000 | D'Urso | 600/407 |
| 6,120,541 A | 9/2000 | Johnson | 623/14.12 |
| 6,120,543 A | 9/2000 | Kubein-Meesenburg et al. | 623/20 |
| 6,126,690 A | 10/2000 | Ateshian et al. | 623/18 |
| 6,139,578 A | 10/2000 | Lee et al. | 623/16.11 |
| 6,146,422 A | 11/2000 | Lawson | 623/17.16 |
| 6,151,521 A | 11/2000 | Guo et al. | 600/407 |
| 6,152,960 A | 11/2000 | Pappas | 623/20.31 |
| 6,156,069 A | 12/2000 | Amstutz | 623/22.11 |
| 6,161,080 A | 12/2000 | Aouni-Ateshian et al. | 703/11 |
| 6,162,208 A | 12/2000 | Hipps | 606/1 |
| 6,165,221 A | 12/2000 | Schmotzer | 623/20.11 |
| 6,171,340 B1 | 1/2001 | McDowell | 623/18.11 |
| 6,175,655 B1 | 1/2001 | George, III et al. | 382/257 |
| 6,178,225 B1 | 1/2001 | Zur et al. | 378/98.2 |
| 6,187,010 B1 | 2/2001 | Masini | 606/86 |
| 6,197,064 B1 | 3/2001 | Haines et al. | 623/20.31 |
| 6,197,325 B1 | 3/2001 | MacPhee et al. | 424/426 |
| 6,200,606 B1 | 3/2001 | Peterson et al. | 424/574 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,249,692 B1 | 6/2001 | Cowin | 600/407 |
| 6,251,143 B1 | 6/2001 | Schwartz et al. | 623/23.72 |
| 6,254,639 B1 | 7/2001 | Peckitt | 623/11.11 |
| 6,261,296 B1 | 7/2001 | Aebi et al. | 606/90 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |
| 6,342,075 B1 | 1/2002 | MacArthur | 623/20.14 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,379,388 B1 | 4/2002 | Ensign et al. | 623/20.34 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,402,786 B1 | 6/2002 | Insall et al. | 623/20.35 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,450,978 B1 | 9/2002 | Brosseau et al. | 600/595 |
| 6,459,948 B1 | 10/2002 | Ateshian et al. | 700/117 |
| 6,468,314 B2 | 10/2002 | Schwartz et al. | 623/23.72 |
| 6,479,996 B1 | 11/2002 | Hoogeveen et al. | 324/309 |
| 6,482,209 B1 | 11/2002 | Engh et al. | 606/79 |
| 6,510,334 B1 | 1/2003 | Schuster et al. | 600/407 |
| 6,514,514 B1 * | 2/2003 | Atkinson et al. | 424/423 |
| 6,520,964 B2 | 2/2003 | Tallarida et al. | 396/567 |
| 6,533,737 B1 | 3/2003 | Brosseau et al. | 600/595 |
| 6,556,855 B2 | 4/2003 | Thesen | 600/419 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |

(56) References Cited

U.S. PATENT DOCUMENTS

| | | |
|---|---|---|
| 6,591,581 B2 | 7/2003 | Schmieding .................... 53/396 |
| 6,592,624 B1 | 7/2003 | Fraser et al. ............... 623/17.16 |
| 6,623,526 B1 | 9/2003 | Lloyd ........................ 623/20.28 |
| 6,626,945 B2 | 9/2003 | Simon et al. ............... 623/17.19 |
| 6,632,235 B2 | 10/2003 | Weikel et al. .................. 606/192 |
| 6,652,587 B2 | 11/2003 | Felt et al. .................. 623/20.16 |
| 6,679,917 B2 | 1/2004 | Ek .............................. 623/20.14 |
| 6,690,816 B2 | 2/2004 | Aylward et al. ............... 382/128 |
| 6,692,448 B2 | 2/2004 | Tanaka et al. .................. 600/587 |
| 6,702,821 B2 | 3/2004 | Bonutti ............................ 606/88 |
| 6,712,856 B1 | 3/2004 | Carignan et al. ........... 623/20.35 |
| 6,719,794 B2 | 4/2004 | Gerber et al. ............... 623/17.11 |
| 6,770,078 B2 | 8/2004 | Bonutti ............................ 606/88 |
| 6,772,026 B2 | 8/2004 | Bradbury et al. ............... 700/98 |
| 6,799,066 B2 | 9/2004 | Steines et al. .................. 600/407 |
| 6,816,607 B2 | 11/2004 | O'Donnell et al. ........... 382/131 |
| 6,835,377 B2 | 12/2004 | Goldberg et al. ........... 424/93.7 |
| 6,855,165 B2 | 2/2005 | Fell et al. .................. 623/14.12 |
| 6,873,741 B2 | 3/2005 | Li ................................ 382/266 |
| 6,893,463 B2 | 5/2005 | Fell et al. .................. 623/14.12 |
| 6,893,467 B1 | 5/2005 | Bercovy .................... 623/20.14 |
| 6,902,582 B2 | 6/2005 | Kubein-Meesenburg et al. ........................... 623/20.31 |
| 6,905,514 B2 | 6/2005 | Carignan et al. ........... 623/20.35 |
| 6,911,044 B2 | 6/2005 | Fell et al. .................. 623/14.12 |
| 6,916,341 B2 | 7/2005 | Rolston ........................ 623/20.3 |
| 6,923,831 B2 | 8/2005 | Fell et al. .................. 623/14.12 |
| 6,932,842 B1 | 8/2005 | Litschko et al. ........... 623/16.11 |
| 6,964,687 B1 | 11/2005 | Bernard et al. ............. 623/17.16 |
| 6,966,928 B2 | 11/2005 | Fell et al. .................. 623/14.12 |
| 6,978,188 B1 | 12/2005 | Christensen ................ 700/118 |
| 6,984,981 B2 | 1/2006 | Tamez-Peña et al. ........ 324/309 |
| 6,998,841 B1 | 2/2006 | Tamez-Peña et al. ........ 324/302 |
| 7,020,314 B1 | 3/2006 | Suri et al. ..................... 382/130 |
| 7,050,534 B2 | 5/2006 | Lang ............................. 378/54 |
| 7,058,159 B2 | 6/2006 | Lang et al. ..................... 378/54 |
| 7,058,209 B2 | 6/2006 | Chen et al. ................... 382/117 |
| 7,060,101 B2 | 6/2006 | O'Connor et al. ......... 623/20.32 |
| 7,105,026 B2 | 9/2006 | Johnson et al. ............ 623/20.14 |
| 7,115,131 B2 | 10/2006 | Engh et al. ..................... 606/79 |
| 7,172,596 B2 | 2/2007 | Coon et al. ..................... 606/87 |
| 7,174,282 B2 | 2/2007 | Hollister et al. ................. 703/2 |
| 7,184,814 B2 | 2/2007 | Lang et al. ................... 600/416 |
| 7,204,807 B2 | 4/2007 | Tsoref ......................... 600/438 |
| 7,238,203 B2 | 7/2007 | Bagga et al. ............... 623/17.11 |
| 7,239,908 B1 | 7/2007 | Alexander et al. ........... 600/427 |
| 7,244,273 B2 | 7/2007 | Pedersen et al. ........... 623/14.12 |
| 7,245,697 B2 | 7/2007 | Lang ............................. 378/54 |
| 7,292,674 B2 | 11/2007 | Lang ............................. 378/54 |
| 7,326,252 B2 | 2/2008 | Otto et al. .................. 623/20.15 |
| 7,379,529 B2 | 5/2008 | Lang ............................. 378/54 |
| 7,438,685 B2 | 10/2008 | Burdette et al. ............. 600/439 |
| 7,467,892 B2 | 12/2008 | Lang et al. ................... 378/207 |
| 7,468,075 B2 | 12/2008 | Lang et al. ................. 623/16.11 |
| 7,517,358 B2 | 4/2009 | Petersen ....................... 606/247 |
| 7,520,901 B2 | 4/2009 | Engh et al. .................. 623/20.21 |
| 7,534,263 B2 | 5/2009 | Burdulis, Jr. et al. ....... 623/14.12 |
| 7,572,293 B2 | 8/2009 | Rhodes et al. ............. 623/20.32 |
| 7,603,192 B2 | 10/2009 | Martin et al. .................... 700/98 |
| 7,611,519 B2 | 11/2009 | Lefevre et al. ................. 606/102 |
| 7,611,653 B1 | 11/2009 | Elsner et al. ................... 264/255 |
| 7,615,054 B1 | 11/2009 | Bonutti ............................ 606/88 |
| 7,618,451 B2 | 11/2009 | Berez et al. ................. 623/14.12 |
| 7,634,119 B2 | 12/2009 | Tsougarakis et al. ........ 382/128 |
| 7,718,109 B2 | 5/2010 | Robb et al. ................... 264/308 |
| 7,796,791 B2 | 9/2010 | Tsougarakis et al. ........ 382/128 |
| 7,799,077 B2 | 9/2010 | Lang et al. .................. 623/14.12 |
| 7,806,896 B1 | 10/2010 | Bonutti ........................ 606/86 R |
| 7,842,092 B2 | 11/2010 | Otto et al. .................... 623/18.11 |
| 7,881,768 B2 | 2/2011 | Lang et al. ................... 600/407 |
| 7,914,582 B2 | 3/2011 | Felt et al. .................. 623/20.16 |
| 7,935,151 B2 | 5/2011 | Haines ....................... 623/20.35 |
| 7,981,158 B2 | 7/2011 | Fitz et al. .................... 623/17.16 |
| 7,983,777 B2 | 7/2011 | Melton et al. .................... 700/98 |
| 8,036,729 B2 | 10/2011 | Lang et al. ................... 600/407 |
| 8,062,302 B2 * | 11/2011 | Lang et al. ....................... 606/87 |
| 8,066,708 B2 | 11/2011 | Lang et al. ....................... 606/88 |
| 8,070,821 B2 | 12/2011 | Roger ........................ 623/20.17 |
| 8,077,950 B2 | 12/2011 | Tsougarakis et al. ......... 382/128 |
| 8,083,745 B2 | 12/2011 | Lang et al. ....................... 606/87 |
| 8,086,336 B2 | 12/2011 | Christensen ................... 700/98 |
| 8,094,900 B2 | 1/2012 | Steines et al. ................. 382/128 |
| 8,105,330 B2 | 1/2012 | Fitz et al. ....................... 606/88 |
| 8,112,142 B2 | 2/2012 | Alexander et al. ............ 600/407 |
| RE43,282 E | 3/2012 | Alexander et al. ............ 600/427 |
| 8,192,498 B2 | 6/2012 | Wagner et al. ............. 623/20.21 |
| 8,211,181 B2 | 7/2012 | Walker ....................... 623/20.21 |
| 8,234,097 B2 | 7/2012 | Steines et al. .................... 703/1 |
| 8,236,061 B2 | 8/2012 | Heldreth et al. ............ 623/20.31 |
| 8,265,730 B2 * | 9/2012 | Alexander et al. ............ 600/410 |
| 8,306,601 B2 | 11/2012 | Lang et al. ................... 600/407 |
| 8,337,501 B2 | 12/2012 | Fitz et al. ..................... 606/86 R |
| 8,337,507 B2 | 12/2012 | Lang et al. ................... 606/102 |
| 8,343,218 B2 | 1/2013 | Lang et al. ................. 623/16.11 |
| 8,366,771 B2 | 2/2013 | Burdulis, Jr. et al. ....... 623/14.12 |
| 8,369,926 B2 | 2/2013 | Lang et al. ................... 600/407 |
| 8,377,129 B2 | 2/2013 | Fitz et al. .................. 623/14.12 |
| 8,439,926 B2 | 5/2013 | Bojarski et al. ................. 606/88 |
| 8,460,304 B2 * | 6/2013 | Fitz et al. ....................... 606/88 |
| 8,480,754 B2 | 7/2013 | Bojarski et al. ............. 623/20.35 |
| 8,500,740 B2 | 8/2013 | Bojarski et al. ............ 606/86 R |
| 8,529,568 B2 | 9/2013 | Bouadi .......................... 606/84 |
| 8,529,630 B2 | 9/2013 | Bojarski et al. ............. 623/20.14 |
| 8,545,569 B2 | 10/2013 | Fitz et al. .................. 623/20.14 |
| 8,551,099 B2 | 10/2013 | Lang et al. ................. 606/86 R |
| 8,551,102 B2 | 10/2013 | Fitz et al. ....................... 606/88 |
| 8,551,103 B2 | 10/2013 | Fitz et al. ....................... 606/88 |
| 8,551,169 B2 | 10/2013 | Fitz et al. .................. 623/14.12 |
| 8,556,906 B2 | 10/2013 | Fitz et al. ....................... 606/87 |
| 8,556,907 B2 | 10/2013 | Fitz et al. ....................... 606/87 |
| 8,556,971 B2 | 10/2013 | Lang ......................... 623/14.12 |
| 8,556,983 B2 | 10/2013 | Bojarski et al. ............ 623/20.35 |
| 8,561,278 B2 | 10/2013 | Fitz et al. ................... 29/407.09 |
| 8,562,611 B2 | 10/2013 | Fitz et al. ....................... 606/80 |
| 8,562,618 B2 | 10/2013 | Fitz et al. ....................... 606/88 |
| 8,568,479 B2 | 10/2013 | Fitz et al. .................. 623/14.12 |
| 8,568,480 B2 | 10/2013 | Fitz et al. .................. 623/14.12 |
| 8,617,172 B2 | 12/2013 | Fitz et al. ....................... 606/88 |
| 8,617,242 B2 | 12/2013 | Philipp ...................... 623/16.11 |
| 8,623,026 B2 | 1/2014 | Wong et al. .................... 606/96 |
| 8,634,617 B2 * | 1/2014 | Tsougarakis et al. ......... 382/128 |
| 8,638,998 B2 | 1/2014 | Steines et al. ................ 382/128 |
| 8,641,716 B2 | 2/2014 | Fitz et al. ....................... 606/80 |
| 8,657,827 B2 | 2/2014 | Fitz et al. ....................... 606/87 |
| 8,682,052 B2 | 3/2014 | Fitz et al. .................... 382/131 |
| 8,690,945 B2 | 4/2014 | Fitz et al. ................... 623/16.11 |
| 8,709,089 B2 | 4/2014 | Lang et al. ................. 623/18.11 |
| 8,735,773 B2 | 5/2014 | Lang ....................... 219/121.72 |
| 8,768,028 B2 | 7/2014 | Lang et al. .................. 382/131 |
| 8,771,365 B2 | 7/2014 | Bojarski et al. ............. 623/20.32 |
| 2001/0001120 A1 | 5/2001 | Masini .......................... 606/86 |
| 2001/0010023 A1 | 7/2001 | Schwartz et al. ........... 623/23.72 |
| 2001/0039455 A1 | 11/2001 | Simon et al. ................ 623/23.51 |
| 2002/0013626 A1 | 1/2002 | Geistlich et al. ............. 623/23.57 |
| 2002/0016543 A1 | 2/2002 | Tyler ............................. 600/410 |
| 2002/0022884 A1 | 2/2002 | Mansmann ................ 623/14.12 |
| 2002/0045940 A1 | 4/2002 | Giannetti et al. ........... 623/11.11 |
| 2002/0052606 A1 | 5/2002 | Bonutti .......................... 606/88 |
| 2002/0059049 A1 | 5/2002 | Bradbury et al. ............... 703/11 |
| 2002/0067798 A1 | 6/2002 | Lang et al. ..................... 378/54 |
| 2002/0068979 A1 | 6/2002 | Brown et al. ................ 623/20.3 |
| 2002/0072821 A1 | 6/2002 | Baker ............................ 700/98 |
| 2002/0082703 A1 | 6/2002 | Repicci ....................... 623/20.29 |
| 2002/0087274 A1 | 7/2002 | Alexander et al. ............ 702/19 |
| 2002/0106625 A1 | 8/2002 | Hung et al. .................... 435/1.1 |
| 2002/0111694 A1 | 8/2002 | Ellingsen et al. ............ 623/23.57 |
| 2002/0115647 A1 | 8/2002 | Halvorsen et al. ........... 514/171 |
| 2002/0120274 A1 | 8/2002 | Overaker et al. ............... 606/72 |
| 2002/0120281 A1 | 8/2002 | Overaker .................... 606/151 |
| 2002/0127264 A1 | 9/2002 | Felt et al. ..................... 424/423 |
| 2002/0133230 A1 | 9/2002 | Repicci ...................... 623/14.12 |
| 2002/0147392 A1 | 10/2002 | Steines et al. ................. 600/407 |
| 2002/0151986 A1 | 10/2002 | Asculai et al. ................ 424/484 |
| 2002/0156150 A1 | 10/2002 | Williams et al. .............. 523/113 |

(56) References Cited

U.S. PATENT DOCUMENTS

| | | | |
|---|---|---|---|
| 2002/0173852 A1 | 11/2002 | Felt et al. | 623/20.32 |
| 2002/0177770 A1 | 11/2002 | Lang et al. | 600/410 |
| 2002/0183850 A1 | 12/2002 | Felt et al. | 623/20.16 |
| 2003/0015208 A1 | 1/2003 | Lang et al. | 128/922 |
| 2003/0031292 A1 | 2/2003 | Lang | 378/54 |
| 2003/0035773 A1 | 2/2003 | Sofia Totterman et al. | 424/9.1 |
| 2003/0045935 A1 | 3/2003 | Angelucci et al. | 623/17.11 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0063704 A1 | 4/2003 | Lang | 378/54 |
| 2003/0069591 A1 | 4/2003 | Carson et al. | 606/130 |
| 2003/0100953 A1 | 5/2003 | Rosa et al. | 623/20.3 |
| 2003/0158606 A1 | 8/2003 | Coon et al. | 623/20.15 |
| 2003/0216669 A1 | 11/2003 | Lang et al. | 600/587 |
| 2003/0225457 A1 | 12/2003 | Justin et al. | 623/20.14 |
| 2003/0236473 A1 | 12/2003 | Dore et al. | 600/587 |
| 2004/0006393 A1 | 1/2004 | Burkinshaw | 623/20.3 |
| 2004/0062358 A1 | 4/2004 | Lang et al. | 378/207 |
| 2004/0081287 A1 | 4/2004 | Lang et al. | 378/210 |
| 2004/0098132 A1 | 5/2004 | Andriacchi et al. | 623/20.35 |
| 2004/0098133 A1 | 5/2004 | Carignan et al. | 623/20.35 |
| 2004/0102851 A1 | 5/2004 | Saladino | 623/20.15 |
| 2004/0102852 A1 | 5/2004 | Johnson et al. | 623/20.15 |
| 2004/0102866 A1 | 5/2004 | Harris et al. | 623/20.35 |
| 2004/0117015 A1 | 6/2004 | Biscup | 623/16.11 |
| 2004/0117023 A1 | 6/2004 | Gerbec et al. | 623/18.11 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0138755 A1 | 7/2004 | O'Connor et al. | 623/20.32 |
| 2004/0147927 A1 | 7/2004 | Tsougarakis et al. | 606/73 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0204766 A1 | 10/2004 | Siebel | 623/20.31 |
| 2004/0236424 A1 | 11/2004 | Berez et al. | 623/14.12 |
| 2005/0010106 A1 | 1/2005 | Lang et al. | 600/425 |
| 2005/0015153 A1 | 1/2005 | Goble et al. | 623/23.46 |
| 2005/0021042 A1 | 1/2005 | Marnay et al. | 606/99 |
| 2005/0033424 A1 | 2/2005 | Fell | 623/14.12 |
| 2005/0043807 A1 | 2/2005 | Wood | 623/20.14 |
| 2005/0055028 A1 | 3/2005 | Haines | 606/79 |
| 2005/0078802 A1 | 4/2005 | Lang et al. | 387/207 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0125029 A1 | 6/2005 | Bernard et al. | 606/205 |
| 2005/0148843 A1 | 7/2005 | Roose | 700/117 |
| 2005/0154471 A1 | 7/2005 | Aram et al. | 623/20.15 |
| 2005/0171612 A1 | 8/2005 | Rolston | 623/20.19 |
| 2005/0203384 A1 | 9/2005 | Sati et al. | 600/426 |
| 2005/0216305 A1 | 9/2005 | Funderud | 705/2 |
| 2005/0226374 A1 | 10/2005 | Lang et al. | 378/54 |
| 2005/0234461 A1 | 10/2005 | Burdulis, Jr. et al. | 606/79 |
| 2005/0267584 A1 | 12/2005 | Burdulis, Jr. et al. | 623/20.19 |
| 2005/0278034 A1 | 12/2005 | Johnson et al. | 623/20.15 |
| 2006/0009853 A1 | 1/2006 | Justin et al. | 623/20.3 |
| 2006/0069318 A1 | 3/2006 | Keaveny et al. | 600/300 |
| 2006/0111722 A1 | 5/2006 | Bouadi | 606/79 |
| 2006/0111726 A1 | 5/2006 | Felt et al. | 606/86 |
| 2006/0129246 A1 | 6/2006 | Steffensmeier | 623/20.29 |
| 2006/0149374 A1 | 7/2006 | Winslow et al. | 623/17.11 |
| 2006/0190086 A1 | 8/2006 | Clemow et al. | 623/20.15 |
| 2006/0210017 A1 | 9/2006 | Lang | 378/54 |
| 2006/0210018 A1 | 9/2006 | Lang | 378/54 |
| 2006/0265078 A1 | 11/2006 | McMinn | 623/20.14 |
| 2007/0015995 A1 | 1/2007 | Lang | 600/407 |
| 2007/0047794 A1 | 3/2007 | Lang et al. | 378/132 |
| 2007/0067032 A1 | 3/2007 | Felt et al. | 623/14.12 |
| 2007/0083266 A1 | 4/2007 | Lang | 623/17.11 |
| 2007/0100462 A1 | 5/2007 | Lang et al. | 623/20.29 |
| 2007/0118055 A1 | 5/2007 | McCombs | 600/587 |
| 2007/0118222 A1 | 5/2007 | Lang | 623/17.12 |
| 2007/0118243 A1 | 5/2007 | Schroeder et al. | 700/118 |
| 2007/0156171 A1 | 7/2007 | Lang et al. | 606/205 |
| 2007/0190108 A1 | 8/2007 | Datta et al. | 424/423 |
| 2007/0198022 A1 | 8/2007 | Lang et al. | 606/88 |
| 2007/0203430 A1 | 8/2007 | Lang et al. | 600/587 |
| 2007/0233156 A1 | 10/2007 | Metzger | 606/130 |
| 2007/0233269 A1 | 10/2007 | Steines et al. | 623/20.21 |
| 2007/0239165 A1 | 10/2007 | Amirouche | 606/86 |
| 2007/0250169 A1 | 10/2007 | Lang | 623/17.12 |
| 2007/0255288 A1 | 11/2007 | Mahfouz et al. | 606/102 |
| 2007/0274444 A1 | 11/2007 | Lang | 378/54 |
| 2007/0276224 A1 | 11/2007 | Lang et al. | 600/410 |
| 2007/0276501 A1 | 11/2007 | Betz et al. | 623/17.16 |
| 2007/0282451 A1 | 12/2007 | Metzger et al. | 623/20.28 |
| 2008/0009950 A1 | 1/2008 | Richardson | 623/20.29 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0119938 A1 | 5/2008 | Oh | 623/20.14 |
| 2008/0119940 A1 | 5/2008 | Otto et al. | 623/20.31 |
| 2008/0147072 A1 | 6/2008 | Park et al. | 606/87 |
| 2008/0170659 A1 | 7/2008 | Lang et al. | 378/56 |
| 2008/0172125 A1 | 7/2008 | Ek | 623/14.12 |
| 2008/0195108 A1 | 8/2008 | Bhatnagar et al. | 606/87 |
| 2008/0195216 A1 | 8/2008 | Philipp | 623/18.11 |
| 2008/0208348 A1 | 8/2008 | Fitz | 623/19.14 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0255445 A1 | 10/2008 | Neubauer et al. | 600/416 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2008/0319448 A1 | 12/2008 | Lavallee et al. | 606/102 |
| 2009/0076371 A1 | 3/2009 | Lang et al. | 600/407 |
| 2009/0076508 A1 | 3/2009 | Weinans et al. | 606/62 |
| 2009/0118830 A1 | 5/2009 | Fell | 623/14.12 |
| 2009/0131941 A1 | 5/2009 | Park et al. | 606/87 |
| 2009/0222103 A1 | 9/2009 | Fitz et al. | 623/18.11 |
| 2009/0226068 A1 | 9/2009 | Fitz et al. | 382/131 |
| 2009/0228111 A1 | 9/2009 | Otto | 623/20.19 |
| 2009/0228113 A1 | 9/2009 | Lang et al. | 623/20.32 |
| 2009/0276045 A1 | 11/2009 | Lang | 623/14.12 |
| 2009/0306676 A1 | 12/2009 | Lang et al. | 606/102 |
| 2009/0312805 A1 | 12/2009 | Lang et al. | 606/86 R |
| 2009/0326666 A1 | 12/2009 | Wyss et al. | 623/20.39 |
| 2010/0054572 A1 | 3/2010 | Tsougarakis et al. | 382/131 |
| 2010/0217270 A1 | 8/2010 | Polinski et al. | 606/87 |
| 2010/0274534 A1 | 10/2010 | Steines et al. | 703/1 |
| 2010/0303313 A1 | 12/2010 | Lang et al. | 382/128 |
| 2010/0303317 A1 | 12/2010 | Tsougarakis et al. | 382/128 |
| 2010/0303324 A1 | 12/2010 | Lang et al. | 382/131 |
| 2010/0305708 A1 | 12/2010 | Lang et al. | 623/20.18 |
| 2010/0305907 A1 | 12/2010 | Fitz et al. | 703/1 |
| 2010/0329530 A1 | 12/2010 | Lang et al. | 382/131 |
| 2010/0331991 A1 | 12/2010 | Wilkinson et al. | 623/20.32 |
| 2011/0029091 A1 | 2/2011 | Bojarski et al. | 623/20.32 |
| 2011/0029093 A1 | 2/2011 | Bojarski et al. | 623/20.35 |
| 2011/0066245 A1 | 3/2011 | Lang et al. | 623/18.11 |
| 2011/0071645 A1 | 3/2011 | Bojarski et al. | 623/20.35 |
| 2011/0071802 A1 | 3/2011 | Bojarski et al. | 703/1 |
| 2011/0087332 A1 | 4/2011 | Bojarski et al. | 623/20.32 |
| 2011/0125009 A1 | 5/2011 | Lang et al. | 600/425 |
| 2011/0144760 A1 | 6/2011 | Wong et al. | 623/20.14 |
| 2011/0218635 A1 | 9/2011 | Amis et al. | 623/20.18 |
| 2011/0264097 A1 | 10/2011 | Hodorek et al. | 606/88 |
| 2011/0266265 A1 | 11/2011 | Lang | 219/121.72 |

(56) References Cited

U.S. PATENT DOCUMENTS

| | | | | |
|---|---|---|---|---|
| 2011/0288669 | A1 | 11/2011 | Sanford et al. | 700/103 |
| 2011/0295378 | A1 | 12/2011 | Bojarski et al. | 623/20.35 |
| 2012/0022659 | A1 | 1/2012 | Wentorf | 623/20.32 |
| 2012/0093377 | A1 | 4/2012 | Tsougarakis et al. | 382/128 |
| 2012/0191205 | A1 | 7/2012 | Bojarski et al. | 623/20.32 |
| 2012/0191420 | A1 | 7/2012 | Bojarski et al. | 703/1 |
| 2012/0197408 | A1 | 8/2012 | Lang et al. | 623/18.11 |
| 2012/0201440 | A1 | 8/2012 | Steines et al. | 382/131 |
| 2012/0209394 | A1 | 8/2012 | Bojarski et al. | 623/20.32 |
| 2012/0232669 | A1 | 9/2012 | Bojarski et al. | 623/20.3 |
| 2012/0232670 | A1 | 9/2012 | Bojarski et al. | 623/20.35 |
| 2012/0232671 | A1 | 9/2012 | Bojarski et al. | 623/20.35 |
| 2012/0265496 | A1 | 10/2012 | Mahfouz | 703/1 |
| 2013/0006598 | A1 | 1/2013 | Alexander et al. | 703/11 |
| 2013/0071828 | A1 | 3/2013 | Lang et al. | 434/274 |
| 2013/0103363 | A1 | 4/2013 | Lang et al. | 703/1 |
| 2013/0110471 | A1 | 5/2013 | Lang et al. | 703/1 |
| 2013/0197870 | A1 | 8/2013 | Steines et al. | 703/1 |
| 2013/0211531 | A1 | 8/2013 | Steines et al. | 623/20.35 |
| 2013/0245803 | A1 | 9/2013 | Lang | 700/98 |
| 2013/0297031 | A1 | 11/2013 | Hafez | 623/20.14 |
| 2014/0005792 | A1 | 1/2014 | Lang et al. | 623/20.32 |
| 2014/0029814 | A1 | 1/2014 | Fitz et al. | 382/128 |
| 2014/0039631 | A1 | 2/2014 | Bojarski et al. | 623/18.11 |
| 2014/0086780 | A1 | 3/2014 | Miller et al. | 419/1 |
| 2014/0109384 | A1 | 4/2014 | Lang | 29/557 |
| 2014/0115872 | A1 | 5/2014 | Steines et al. | 29/592 |
| 2014/0136154 | A1 | 5/2014 | Bojarski et al. | 703/1 |
| 2014/0172111 | A1 | 6/2014 | Lang et al. | 623/20.32 |
| 2014/0194996 | A1 | 7/2014 | Bojarski et al. | 623/20.35 |
| 2014/0207243 | A1 | 7/2014 | Fitz et al. | 623/20.16 |
| 2014/0208578 | A1 | 7/2014 | Linderman et al. | 29/592 |

FOREIGN PATENT DOCUMENTS

| | | | |
|---|---|---|---|
| CN | 101288597 | 10/2008 | A61B 17/56 |
| DE | 2306552 | 8/1974 | A61F 1/00 |
| DE | 3516743 | 11/1986 | A61F 2/36 |
| DE | 8909091 | 9/1989 | A61F 2/35 |
| DE | 44 34 539 | 4/1996 | A61F 2/38 |
| DE | 19803673 | 8/1999 | A61L 27/54 |
| DE | 19926083 | 12/2000 | A61L 27/54 |
| DE | 10135771 | 2/2003 | A61B 17/70 |
| EP | 0528080 | 2/1993 | A61F 2/30 |
| EP | 0600806 | 6/1994 | A61L 25/00 |
| EP | 0672397 | 9/1995 | A61F 2/38 |
| EP | 0 704 193 | 4/1996 | A61F 2/30 |
| EP | 0626156 | 7/1997 | A61F 2/38 |
| EP | 0613380 | 12/1999 | A61L 27/00 |
| EP | 1074229 | 2/2001 | A61F 2/38 |
| EP | 1077253 | 2/2001 | C12N 5/00 |
| EP | 1120087 | 8/2001 | A61B 17/06 |
| EP | 1129675 | 9/2001 | A61F 2/30 |
| EP | 0732091 | 12/2001 | A61F 2/38 |
| EP | 0896825 | 7/2002 | A61L 27/00 |
| EP | 0814731 | 8/2002 | A61F 2/30 |
| EP | 1234552 | 8/2002 | A61F 2/00 |
| EP | 1234555 | 8/2002 | A61F 2/30 |
| EP | 0809987 | 10/2002 | A61F 2/38 |
| EP | 0833620 | 10/2002 | A61K 9/22 |
| EP | 1327423 | 7/2003 | A61F 2/38 |
| EP | 1329205 | 7/2003 | A61F 2/38 |
| EP | 0530804 | 6/2004 | A61L 25/00 |
| EP | 1437101 | 7/2004 | A61F 2/08 |
| EP | 1070487 | 9/2005 | A61F 2/08 |
| EP | 1886640 | 2/2008 | A61B 19/00 |
| EP | 2324799 | 5/2011 | A61F 2/38 |
| EP | 2173260 | 1/2012 | A61B 17/15 |
| FR | 2589720 | 11/1985 | A61F 2/38 |
| FR | 2740326 | 4/1997 | A61F 2/38 |
| GB | 1451283 | 9/1976 | A61F 1/24 |
| GB | 2291355 | 1/1996 | A61F 2/38 |
| GB | 2304051 | 3/1997 | A61F 2/38 |
| GB | 2348373 | 10/2000 | A61F 2/38 |
| JP | 56-083343 | 7/1981 | A61F 1/03 |
| JP | 61-247448 | 11/1986 | A61F 2/30 |
| JP | 1-249049 | 10/1989 | A61F 2/38 |
| JP | 05-184612 | 7/1993 | A61F 2/30 |
| JP | 7-236648 | 9/1995 | A61F 2/28 |
| JP | 8-173465 | 7/1996 | A61F 2/38 |
| JP | 9-206322 | 8/1997 | A61F 2/36 |
| JP | 11-19104 | 1/1999 | A61F 2/28 |
| JP | 11-276510 | 10/1999 | A61F 2/28 |
| JP | 2007-521881 | 8/2007 | A61F 2/44 |
| WO | WO 87/02882 | 5/1987 | A61F 2/38 |
| WO | WO 90/09769 | 9/1990 | A61F 2/28 |
| WO | WO 92/03108 | 3/1992 | A61F 2/38 |
| WO | WO 93/04710 | 3/1993 | A61L 25/00 |
| WO | WO 93/09819 | 5/1993 | A61L 27/00 |
| WO | WO 93/25157 | 12/1993 | A61B 17/56 |
| WO | WO 95/27450 | 10/1995 | A61F 2/38 |
| WO | WO 95/28688 | 10/1995 | G06T 15/00 |
| WO | WO 95/30390 | 11/1995 | A61F 2/38 |
| WO | WO 95/32623 | 12/1995 | A01N 1/02 |
| WO | WO 96/24302 | 8/1996 | A61B 17/90 |
| WO | WO 97/25942 | 7/1997 | A61F 2/32 |
| WO | WO 97/27885 | 8/1997 | A61L 27/00 |
| WO | WO 97/29703 | 8/1997 | A61B 17/56 |
| WO | WO 97/38676 | 10/1997 | A61K 9/10 |
| WO | WO 97/46665 | 12/1997 | C12N 5/06 |
| WO | WO 98/08469 | 3/1998 | A61F 2/30 |
| WO | WO 98/12994 | 4/1998 | A61F 2/28 |
| WO | WO 98/20816 | 5/1998 | A61F 2/38 |
| WO | WO 98/30617 | 7/1998 | C08G 63/12 |
| WO | WO 98/52498 | 11/1998 | A61F 2/28 |
| WO | WO 99/02654 | 1/1999 | C12N 5/00 |
| WO | WO 99/08598 | 2/1999 | A61B 8/00 |
| WO | WO 99/08728 | 2/1999 | A61L 27/00 |
| WO | WO 99/42061 | 8/1999 | A61F 2/38 |
| WO | WO 99/47186 | 9/1999 | A61L 27/00 |
| WO | WO 99/51719 | 10/1999 | C12M 3/00 |
| WO | WO 00/09179 | 2/2000 | A61L 25/00 |
| WO | WO 00/15153 | 3/2000 | A61F 2/38 |
| WO | WO 00/19911 | 4/2000 | A61B 17/02 |
| WO | WO 00/35346 | 6/2000 | A61B 5/11 |
| WO | WO 00/48550 | 8/2000 | |
| WO | WO 00/59411 | 10/2000 | A61F 2/38 |
| WO | WO 00/68749 | 11/2000 | G05B 19/4099 |
| WO | WO 00/74554 | 12/2000 | |
| WO | WO 00/74741 | 12/2000 | A61L 27/00 |
| WO | WO 00/76428 | 12/2000 | A61F 2/38 |
| WO | WO 01/10356 | 2/2001 | A61F 2/46 |
| WO | WO 01/17463 | 3/2001 | A61F 2/30 |
| WO | WO 01/19254 | 3/2001 | A61B 17/00 |
| WO | WO 01/35968 | 5/2001 | A61K 35/00 |
| WO | WO 01/45764 | 6/2001 | A61L 27/36 |
| WO | WO 01/68800 | 9/2001 | C12M 3/00 |
| WO | WO 01/70142 | 9/2001 | A61F 2/38 |
| WO | WO 01/77988 | 10/2001 | A61F 2/38 |
| WO | WO 01/82677 | 11/2001 | |
| WO | WO 01/91672 | 12/2001 | A61F 2/36 |
| WO | WO 02/02021 | 1/2002 | A61B 17/56 |
| WO | WO 02/09623 | 2/2002 | A61F 2/38 |
| WO | WO 02/22013 | 3/2002 | A61B 5/55 |
| WO | WO 02/22014 | 3/2002 | A61B 5/55 |
| WO | WO 02/23483 | 3/2002 | A61B 5/55 |
| WO | WO 02/34310 | 5/2002 | A61L 31/04 |
| WO | WO 02/36147 | 5/2002 | A61K 31/04 |
| WO | WO 02/37423 | 5/2002 | G06T 17/00 |
| WO | WO 02/061688 | 8/2002 | G06T 17/00 |
| WO | WO 02/096268 | 12/2002 | |
| WO | WO 03/007788 | 1/2003 | |
| WO | WO 03/013373 | 2/2003 | A61B 17/17 |
| WO | WO 03/037192 | 5/2003 | A61B 17/15 |
| WO | WO 03/047470 | 6/2003 | A61F 2/34 |
| WO | WO 03/051210 | 6/2003 | A61B 17/58 |
| WO | WO 03/061522 | 7/2003 | |
| WO | WO 03/099106 | 12/2003 | |
| WO | WO 2004/006811 | 1/2004 | A61F 2/46 |
| WO | WO 2004/032806 | 4/2004 | A61F 2/30 |
| WO | WO 2004/043305 | 5/2004 | A61F 2/30 |
| WO | WO 2004/049981 | 6/2004 | A61F 2/46 |
| WO | WO 2004/051301 | 6/2004 | G01R 33/56 |

(56) References Cited

FOREIGN PATENT DOCUMENTS

| | | | |
|---|---|---|---|
| WO | WO 2004/073550 | 9/2004 | |
| WO | WO 2005/002473 | 1/2005 | ............... A61F 2/38 |
| WO | WO 2005/016175 | 2/2005 | |
| WO | WO 2005/020850 | 3/2005 | |
| WO | WO 2005/051239 | 6/2005 | ............... A61F 2/08 |
| WO | WO 2005/051240 | 6/2005 | ............... A61F 2/08 |
| WO | WO 2005/067521 | 7/2005 | |
| WO | WO 2005/076974 | 8/2005 | |
| WO | WO 2006/012370 | 2/2006 | ............ B65D 45/04 |
| WO | WO 2006/058057 | 6/2006 | ............... A61F 2/38 |
| WO | WO 2006/060795 | 6/2006 | ............ A61B 17/17 |
| WO | WO 2006/065774 | 6/2006 | ............... A61F 2/44 |
| WO | WO 2006/092600 | 9/2006 | ............ A61B 19/00 |
| WO | WO 2007/041375 | 4/2007 | ............... A61F 2/38 |
| WO | WO 2007/062079 | 5/2007 | ............... A61F 2/30 |
| WO | WO 2007/092841 | 8/2007 | ............ A61B 17/15 |
| WO | WO 2007/106172 | 9/2007 | ............... A61F 2/38 |
| WO | WO 2007/109641 | 9/2007 | ............... A61F 2/30 |
| WO | WO 2008/021494 | 2/2008 | ............ G06F 19/00 |
| WO | WO 2008/055161 | 5/2008 | ............... A61F 2/44 |
| WO | WO 2008/101090 | 8/2008 | ............... A61F 2/38 |
| WO | WO 2008/117028 | 10/2008 | ............ A61B 17/15 |
| WO | WO 2008/157412 | 12/2008 | ............ A61B 17/17 |
| WO | WO 2009/068892 | 6/2009 | ............... A61C 9/00 |
| WO | WO 2009/140294 | 11/2009 | ............... A61F 2/30 |
| WO | WO 2010/099231 | 9/2010 | ............ A61B 2/38 |
| WO | WO 2010/099353 | 9/2010 | ............... A61F 2/30 |
| WO | WO 2010/140036 | 12/2010 | ............... A61F 2/38 |
| WO | WO 2010/151564 | 12/2010 | ............... A61F 2/38 |
| WO | WO 2011/028624 | 3/2011 | ............... A61F 2/38 |
| WO | WO 2011/056995 | 5/2011 | ............... A61F 2/38 |
| WO | WO 2011/072235 | 6/2011 | ............... A61F 2/38 |
| WO | WO 2011/075697 | 6/2011 | ............... A61F 2/46 |
| WO | WO 2012/112694 | 8/2012 | ............... A61B 6/00 |
| WO | WO 2012/112698 | 8/2012 | ............... A61F 2/30 |
| WO | WO 2012/112701 | 8/2012 | ............... A61F 2/30 |
| WO | WO 2012/112702 | 8/2012 | ............... A61F 2/30 |
| WO | WO 2013/020026 | 2/2013 | ............... A61F 2/30 |
| WO | WO 2013/025814 | 2/2013 | ............... A61F 2/38 |
| WO | WO 2013/056036 | 4/2013 | ............... A61F 2/38 |
| WO | WO 2013/131066 | 9/2013 | ............... A61F 2/38 |
| WO | WO 2013/152341 | 10/2013 | ............... A61F 2/38 |
| WO | WO 2014/035991 | 3/2014 | ............ A61B 17/56 |

OTHER PUBLICATIONS

Sunstein Kann Murphy & Timbers LLP, Response to Office Action dated Feb. 3, 2011, pertaining to U.S. Appl. No. 12/614,946, 25 pages.
United States Patent and Trademark Office, Notice of Allowance dated Sep. 29, 2011, pertaining to U.S. Appl. No. 12/614,946, 28 pages.
United States Patent and Trademark Office, Office Action dated Nov. 7, 2012, pertaining to U.S. Appl. No. 13/345,843, 18 pages.
Sunstein Kann Murphy & Timbers LLP, Amendment dated May 7, 2013 pertaining to U.S. Appl. No. 13/345,843, 31 pages.
United States Patent and Trademark Office, Notice of Allowance dated May 30, 2013, pertaining to U.S. Appl. No. 13/345,843, 36 pages.
United States Patent and Trademark Office, Office Action dated Oct. 11, 2012, pertaining to U.S. Appl. No. 13/312,339, 32 pages.
Sunstein Kann Murphy & Timbers LLP, Amendment dated Apr. 11, 2013, pertaining to U.S. Appl. No. 13/312,339, 11 pages.
United States Patent and Trademark Office, Notice of Allowance dated May 31, 2013, pertaining to U.S. Appl. No. 13/312,339, 53 pages.
International Searching Authority, International Search Report—International Application No. PCT/US2010/061141, dated Aug. 31, 2011, together with the Written Opinion of the International Searching Authority, 8 pages.
European Patent Office, Extended European Search Report—Application No. 10836760.8-1654 dated Apr. 11, 2014, 6 pages.

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.
Adam et al., "MR Imaging of the Knee: Three-Dimensional Volume Imaging Combined with Fast Processing," J. Compt. Asst. Tomogr., 13(6): 984-988 (1989).
Adams et al., "Quantitative Imaging of Osteoarthritis," Semin Arthritis Rheum, 20(6) Suppl. 2: 26-39 (Jun. 1991).
Ahmad et al., "Biomechanical and Topographic Considerations for Autologous Osteochondral Grafting in the Knee," Am J Sports Med, 29(2): 201-206 (Mar.-Apr. 2001).
Alexander, "Estimating the motion of bones from markers on the skin," University of Illinois at Chicago (Doctoral Dissertation) (1998).
Alexander et al., "Correcting for deformation in skin-based marker systems," Proceedings of the 3rd Annual Gait and Clinical Movement Analysis Meeting, San Diego, CA (1998).
Alexander et al., "Internal to external correspondence in the analysis of lower limb bone motion," Proceedings of the 1999 ASME Summer Bioengineering Conference, Big Sky, Montana (1999).
Alexander et al., "State estimation theory in human movement analysis," Proceedings of the ASME International Mechanical Engineering Congress (1998).
Alexander et al., "Optimization techniques for skin deformation correction," International Symposium on 3-D Human Movement Conference, Chattanooga, TN, (1998).
Alexander et al., "Dynamic Functional Imaging of the Musculoskeletal System," ASME Winter International Congress and Exposition, Nashville, TN (1999).
Allen et al., "Late degenerative changes after meniscectomy 5 factors affecting the knee after operations," J Bone Joint Surg 66B: 666-671 (1984).
Alley et al., "Ultrafast contrast-enhanced three dimensional MR Aagiography: State of the art," Radiographics 18: 273-285 (1998).
Andersson et al., "MacIntosh Arthroplasty in Rheumatoid Arthritis," Acta. Orthrop. Scand. 45(2):245-259 (1974).
Andriacchi, "Dynamics of knee Malalignment," Orthop Clin North Am 25: 395-403 (1994).
Andriacchi, et al., "A point cluster method for in vivo motion analysis: Applied to a study of knee kinematics," J. Biomech Eng 120(12): 743-749 (1998).
Andriacchi, et al., "Methods for evaluating the progression of Osterarthiritis," Journal of Rehabilitation Research and Development 37(2): 163-170 (2000).
Andriacchi et al., "Gait analysis as a tool to assess joint kinetics biomechanics of normal and pathological human articulating joints," Nijhoff, Series E 93: 83-102 (1985).
Andriacchi et al., "In vivo measurement of six-degrees-of-freedom knee movement during functional testing," Transactions of the Orthopedic Research Society 698 (1995).
Argenson et al., "Is There a Place for Patellofemoral Arthroplasty?," Clinical Orthopaedics and Related Research No. 321, pp. 162-167 (1995).
Aro et al., "Clinical Use of Bone Allografts," Ann Med 25:403-412 (1993).
Bashir, "Validation of Gadolinium-Enhanced MRI of FAF Measurement in Human Cartilage," Intl. Soc. Mag. Resonance Med. (1998).
Beaulieu et al., "Glenohumeral relationships during physiological shoulder motion and stress testing: Initial experience with open MRI and active Scan-25 plane registration," Radiology (1999).
Beaulieu et al., "Dynamic imaging of glenohumeral instability with open MRI," Int. Society for Magnetic Resonance in Medicine Sydney, Australia (1998).
Beckmann et al., "Noninvasive 3D MR Microscopy as Tool in Pharmacological Research: Application to a Model of Rheumatoid Arthritis," Magn Reson Imaging 13(7): 1013-1017 (1995).
Billet, Philippe, French Version—"Gliding Knee Prostheses—Analysis of Mechanical Failures", Thesis, Medical School of Marseilles, 1982, 64 pages.
Billet, Philippe, Translated Version—"Gliding Knee Prostheses—Analysis of Mechanical Failures", Thesis, Medical School of Marseilles, 1982, 93 pages.

(56) References Cited

OTHER PUBLICATIONS

Blazina et al., "Patellofemoral replacement: Utilizing a customized femoral groove replacement," 5(1)53-55 (1990).
Blum et al., "Knee Arthroplasty in Patients with Rheumatoid Arthritis," Ann. Rheum. Dis. 33 (1): 1-11 (1974).
Bobic, "Arthroscopic osteochondral autogaft transplantation in anterior cruciate ligament reconstruction: a preliminary clinical study," Knee Surg Sports Traumatol Arthrosc 3(4): 262-264 (1996).
Boe et al., "Arthroscopic partial meniscectomy in patients aged over 50," J. Bone Joint Surg 68B: 707 (1986).
Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).
Borthakur et al., "In Vivo Triple Quantum Filtered Sodium MRI of Human Articular Cartilage," Proc. Intl. Soc. Mag. Resonance Med., 7:549 (1999).
Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
CAOS, "MIS meets CAOS Spring 2005 Symposium Schedule", *CAOS Spring 2005 Symposium*, pp. 1-9, May 19, 2005.
Carano et al., "Estimation of Erosive Changes in Rheumatoid Arthritis by Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Castriota-Scanderbeg et al., "Precision of Sonographic Measurement of Articular Cartilage: Inter- and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).

Chelule et al., "Patient-Specific Template to Preserve Bone Stock in Total Knee Replacement: Preliminary Results", *15th Annual ISTA Symposium*, Sep. 2002, 1 page.
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).
Cohen et al., "Knee cartilage topography, thickness, and contact areas from MRI: in-vitro calibration and in-vivo measurements," Osteoarthritis and Cartilage 7: 95-109 (1999).
Cohen et al., "Computer-Aided Planning of Patellofemoral Joint OA Surgery: Developing Physical Models from Patient MRI", MICCAI, Oct. 11-13, 1998, 13 pages.
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "Entropy Mapping of Articular Cartilage", ISMRM Seventh Scientific Meeting, Philadelphia, PA (1999) T. 41, V. II.
Dardzinski et al., "T1-T2 Comparison in Adult Articular Cartilage," ISMRM Seventh Scientific Meeting, Philadelphia, PA (May 22-28, 1999).
De Winter et al., "The Richards Type II Patellofemoral Arthroplasty", Acta Orthop Scand 2001; 72 (5): 487-490.
Delp et al., "A Graphics-Based Software System to Develop and Analyze Models of Musculoskeletal Structures," Comput. Biol. Med., vol. 25, No. 1, pp. 21-34, 1995.
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Rheumatology, Oxford University Press 959-983 (1993).
Dougados et al., "Longitudinal radiologic evaluation of osteoarthritis of the knee," J Rheumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).

(56) References Cited

OTHER PUBLICATIONS

Eckstein et al., "In Vivo Reproducibility of Three-Dimensional Cartilage Volume and Thickness Measurements With MR Imaging", AJR 170(3): 593-597 (1998).

Eckstein et al., "New Quantitative Approaches With 3-D MRI: Cartilage Morphology, Function and Degeneration", Medical Imaging International, Nov.-Dec. 1998.

Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).

Eckstein et al., Accuracy of Cartilage Volume and Thickness Measurements with Magnetic Resonance Imaging, Clin. Orthop. 1998; 352: 137-148 T. 60 V. II.

Eckstein et al., "Magnetic Resonance Chondro-Crassometry (MR CCM): A Method for Accurate Determination of Articular Cartilage Thickness?" Magn. Reson. Med. 35: 89-96 (1996).

Eckstein et al., "The Influence of Geometry on the Stress Distribution in Joints—A Finite Element Analysis," Anat Embryol, 189: 545-552 (1994).

Eckstein et al., "The Morphology of Articular Cartilage Assessed by Magnetic Resonance Imaging: Reproducibility and Anatomical Correlation," Sur. Radiol Anat 16: 429-438 (1994).

Elting et al., "Unilateral frame distraction: proximal tibial valgus osteotomy for medial gonarthritis," Contemp Orthop 27(6): 522-524 (1993).

Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).

Faber et al., "Quantitative Changes of Articular Cartilage Microstructure During Compression of an Intact Joint," Proc. Intl. Soc. Mag. Resonance Med., 7:547 (1999).

Falcao et al., "User-steered image segmentation paradigms. Live wire and live lane," Graphical Models and Image Processing 60: 233-260 (1998).

Felson et al., "Weight Loss Reduces the risk for symptomatic knee osteoarthritis in women: the Framingham study," Ann Intern Med 116: 535-539 (1992).

Gandy et al., "One-Year Longitudinal Study of Femoral Cartilage Lesions in Knee Arthritis," Proc. Intl. Soc. Mag. Resonance Med., 7:1032 (1999).

Garrett, "Osteochondral allografts for reconstruction of articular defects of the knee," Instr Course Lect 47: 517-522 (1998).

Gerscovich, "A Radiologist's Guide to the Imaging in the Diagnosis and Treatment of Developmental Dysplasia of the Hip," Skeletal Radiol 26: 447-456 (1997).

Ghelman et al., "Kinematics of the Knee After Prosthetic Replacements", Clin. Orthop. May 1975: (108): 149-157.

Ghosh et al., "Watershed Segmentation of High Resolution Articular Cartilage Images for Assessment of Osteoarthritis," International Society for Magnetic Resonance in Medicine, Philadelphia, (1999).

Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).

Goodwin et al., "MR Imaging of Articular Cartilage: Striations in the Radial Layer Reflect the Fibrous Structure of Cartilage," Proc. Intl. Soc. Mag. Resonance Med., 7:546 (1999).

Gouraud, "Continuous shading of curved surfaces," IEEE Trans on Computers C-20(6) (1971).

Graichen et al., "Three-Dimensional Analysis of the Width of the Subacromial Space in Healthy Subjects and Patients With Impingement Syndrome," American Journal of Roentgenology 172: 1081-1086 (1999).

Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).

Hafez et al., "Computer-assisted Total Knee Arthroplasty Using Patient-specific Templating," *Clinical Orthopaedics and Related Research*, No. 444, pp. 184-192 (Mar. 2006).

Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).

Hardy et al., "Measuring the Thickness of Articular Cartilage From MR Images," J. Magnetic Resonance Imaging 13: 120-126 (2001).

Hardy et al., "The Influence of the Resolution and Contrast on Measuring the Articular Cartilage Volume in Magnetic Resonance Images" Magn Reson Imaging. 18(8): 965-972 (Oct. 2000).

Hargreaves et al., "MR Imaging of Articular Cartilage Using Driven Equilibrium," Magnetic Resonance in Medicine 42(4): 695-703 (Oct. 1999).

Hargreaves et al., "Technical considerations for DEFT imaging," International Society for Magnetic Resonance in Medicine, Sydney, Australia (Apr. 17-24, 1998).

Hargreaves et al., "Imaging of articular cartilage using driven equilibrium," International Society for Magnetic Resonance in Medicine, Sydney, Australia (Apr. 17-24, 1998).

Harryson et al., "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.

Hastings et al., "Double Hemiarthroplasty of the Knee in Rheumatoid Arthritis, A Survey of Fifty Consecutive Cases," J. Bone Joint Surg. Br. 55(1):112-118 (1973).

Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).

Haut et al., "A High Accuracy Three-Dimensional Coordinate Digitizing System for Reconstructing the Geometry of Diarthrodial Joints," J. Biomechanics 31: 571-577 (1998).

Hayes et al., "Evaluation of Articular Cartilage: Radiographic and Cross-Sectional Imaging Techniques," Radiographics 12: 409-428 (1992).

Henderson et al., "Experience with the Use of the Macintosh Prosthesis in Knees of Patients with Pheumatoid Arthritis," South. Med. J. 62(11):1311-1315 (1969).

Henkelman, "Anisotropy of NMR Properties of Tissues", Magn Res Med. 32: 592-601 (1994).

Herberhold et al., "An MR-Based Technique for Quantifying the Deformation of Articular Cartilage During Mechanical Loading in an Intact Cadaver Joint," Magnetic Resonance in Medicine 39(5): 843-850 (1998).

Herberhold, "In Situ Measurement of Articular Cartilage Deformation in Intact Femorapatellar Joints Under Static Loading", Journal of biomechanics 32: 1287-1295 (1999).

Herrmann et al., "High Resolution Imaging of Normal and Osteoarthritic Cartilage with Optical Coherence Tomogrqaphy," J. Rheumatoil 26: 627-635 (1999).

High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).

Hohe, "Surface Size, Curvature Analysis, and Assessment of Knee Joint Incongruity With MR Imaging In Vivo", Magnetic Resonance in Medicine, 47: 554-561 (2002).

Holdsworth et al., "Benefits of Articular Cartilage Imaging at 4 Tesla: An In Vivo Study of Normal Volunteers," Proc. Intl. Soc. Mag. Resonance Med., 7:1028 (1999).

Hughes et al., "Technical Note: A Technique for Measuring the Surface Area of Articular Cartilage in Acetabular Fractures," Br. J. Radiol; 67: 584-588 (1994).

Husmann et al., "Three-Dimensional Morphology of the Proximal Femur," J. Arthroplasty; 12(4): 444-450 (Jun. 1997).

Hyhlik-Durr et al., "Precision of Tibial Cartilage Morphometry with a coronal water-excitation MR sequence," European Radiology 10(2): 297-303 (2000).

Ihara H., "Double-Contrast CT Arthrography of the Cartilage of the Patellofemoral Joint," Clin. Orthop.; 198: 50-55 (Sep. 1985).

(56) References Cited

OTHER PUBLICATIONS

Iida et al., "Socket Location in Total Hip Replacement: Preoperative Computed Tomography and Computer Simulation" Acta Orthop Scand; 59(1): 1-5 (1998).

Irarrazabal et al., "Fast three-dimensional magnetic resonance imaging," Mag Res. Med. 33: 656-662 (1995).

Jessop et al., "Follow-up of the MacIntosh Arthroplasty of the Knee Joint," Rheumatol Phys. Med. 11(5):217-224 (1972).

Johnson et al., "The distribution of load across the knee. A comparison of static and dynamic measurements," J. Bone Joint Surg 62B: 346-349 (1980).

Johnson, "In vivo contact kinematics of the knee joint: Advancing the point cluster technique," Ph.D. Thesis, University of Minnesota (1999).

Johnson et al., "Development of a knee wear method based on prosthetic in vivo slip velocity," Transaction of the Orthopedic Research Society, 46th Annual Meeting (Mar. 2000).

Jonsson et al., "Precision of Hyaline Cartilage Thickness Measurements," Acta Radiol 1992; 33(3): 234-239 (1992).

Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).

Karvonen et al., "Articular Cartilage Defects of the Knee: Correlation Between Magnetic Resonance Imaging and Gross Pathology," Ann Rheum Dis. 49: 672-675 (1990).

Kass et al., "Snakes: Active contour models.," Int J Comput Vision 1: 321-331 (1988).

Kates, et al., "Experiences of Arthroplasty of the Rheumatoid Knee Using MacIntosh Prostheses," Ann. Rheum. Dis. 28(3):328 (1969).

Kaufman et al., "Articular Cartilage Sodium content as a function of compression" Seventh Scientific Meeting of ISMRM, p. 1022, 1999 T. 105, V. III.

Kay et al., The MacIntosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Klosterman et al., "T2 Measurements in Adult Patellar Cartilage at 1.5 and 3.0 Tesla," ISMRM Seventh Scientific Meeting, Philadelphia, PA, (May 22-28, 1999).

Knauss et al., "Self-Diffusion of Water in Cartilage and Cartilage Components as Studied by Pulsed Field Gradient NMR," Magnetic Resonance in Medicine 41:285-292 (1999).

Koh et al., "Visualization by Magnetic Resonance Imaging of Focal Cartilage Lesions in the Excised Mini-Pig Knee," J. Orthop. Res; 14(4): 554-561 (Jul. 1996).

Korhonen et al., "Importance of the Superficial Tissue Layer for the Indentation Stiffness of Articular Cartilage," Med. Eng. Phys; 24(2): 99-108 (Mar. 2002).

Korkala et al., "Autogenous Osteoperiosteal Grafts in the Reconstruction of Full-Thickness Joint Surface Defects," Int. Orthop.; 15(3): 233-237 (1991).

Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).

Kwak et al., "Anatomy of Human Patellofemoral Joint Articular Cartilage: Surface Curvature Analysis," J. Orthop. Res.; 15: 468-472 (1997).

LaFortune et al., "Three dimensional kinematics of the human knee during walking," J. Biomechanics 25: 347-357 (1992).

Lam et al., "X-Ray Diagnosis: A Physician's Approach", Editor Lam, 1998, Springer-Verlag publishers, Title page and Index Only (ISBN 9813083247).

Lang et al., "Functional joint imaging: a new technique integrating MRI and biomotion studies," International Society for Magnetic Resonance in Medicine, Denver (Apr. 18-24, 2000).

Lang et al., Risk factors for progression of cartilage loss: a longitudinal MRI study. European Society of Musculoskeletal Radiology, 6th Annual Meeting, Edinburgh, Scotland (1999).

Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).

Ledingham et al., "Factors affecting radiographic progression of knee osteoarthritis," Ann Rheum Dis 54: 53-58 (1995).

Leenslag et al., "A Porous Composite for Reconstruction of Meniscus Lesions," Biological and Biomechanical Perform. of Biomaterials, Elsevier Science Publishers Amsterdam pp. 147-152 (1986).

Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).

Li et al., A Boundary Optimization Algorithm for Delineating Brain Objects from CT Scans: Nuclear Science Symposium and Medical Imaging Conference 1993 IEEE Conference Record, San Francisco, CA (1993).

Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).

Lombardi, Jr. et al., "Patient-Specific Approach in Total Knee Arthroplasty", Orthopedics, vol. 31, Issue 9, Sep. 2008, 8 pages.

Lorensen et al., "Marching cubes: a high resolution 3d surface construction algorithm," Comput Graph 21: 163-169 (1987).

Losch et al., "A non-invasive technique for 3-dimensional assessment of articular cartilage thickness based on MRI part 1: development of a computational method," Magn Res Imaging 15(7): 795-804 (1997).

Lu et al., "Bone position estimation from skin marker co-ordinates using globals optimization with joint constraints," J Biomechanics 32: 129-134 (1999).

Lu et al., "In vitro degradation of porous poly(L-lactic acid) foams", Biomaterials, 21(15):1595-1605, Aug. 2000.

Lucchetti et al., "Skin movement artefact assessment and compensation in the estimation of knee-joint kinematics," J Biomechanics 31: 977-984 (1998).

Lusse et al., "Measurement of Distribution of Water Content of Human Articular Cartilage Based on Transverse Relaxation Times: An In Vitro Study," Seventh Scientific Meeting of ISMRM, p. 1020 (1999).

Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).

MacIntosh, "Arthroplasty of the Knee in Rheumatoid Arthritis," Proceedings and Reports of Councils and Assotions, J. Bone & Joint Surg., vol. 48B No. (1): 179 (Feb. 1966).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

MacIntosh, "Hemiarthroplasty of the Knee Using a Space Occupying Prosthesis for Painful Varus and Valgus Deformities," J. Bone Joint Surg. Am. Dec. 1958:40-A:1431.

Maki et al., "SNR improvement in NMR microscopy using DEFT," J Mag Res; pp. 482-492 (1988).

Marler et al., "Soft-Tissue Augmentation with Injectable Alginate and Syngeneic Fibroblasts", Plastic & Reconstructive Surgery, 105(6):2049-2058, May 2000.

Marshall et al., "Quantitation of Articular Cartilage Using Magnetic Resonance Imaging and Three-Dimensional Reconstruction," J. Orthop. Res.; 13: 814-823 (1995).

Matsen, III et al., "Robotic Assistance in Orthopaedic Surgery: A Proof of Principle Using Distal Femoral Arthroplasty", Clinical Ortho. and Related Research, 296:178-186 (1993).

Mattila et al., "Massive Osteoarticular Knee Allografts: Structural Changes Evaluated with CT," Radiology; 196: 657-660 (1995).

(56) References Cited

OTHER PUBLICATIONS

McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly for Hetero-Nuclear Investigations of Human Breast at 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Overhoff et al., "Total Knee Arthroplasty: Coordinate System Definition and Planning Based on 3-D Ultrasound Image Volumes", CARS 2001, pp. 283-288.
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the metacarpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).

Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment of Cartilage Volume in the Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte

(56) References Cited

OTHER PUBLICATIONS

LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo Flash MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robinson et al., "The Early Innovators of Today's Resurfacing Condylar Knees", The Journal of Arthroplasty, vol. 20, No. 1, Suppl. 1, 2005.
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an -dimensional digitized picture with applications," Pattern Recognition 27(11): 1551-1565 (1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schipplein et al., "Interaction between active and passive knee stabilizers during level walking," J Orthop Res 9: 113-119 (1991).
Schorn et al., "MacIntosh Arthroplasty in Rheumatoid Arthritis," Rheumatol Rehabil. Aug. 1978:17(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: An Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Slone et al., "Body CT: A Practical Approach", Editor Slone, 1999 McGraw-Hill publishers, Title page and Table of Contents pgs. Only (ISBN 007058219).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method for Quantifying Time Dependent Changes in MR Signal Intensity of Articular Cartilage as a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Stout et al., "X-Ray Structure Determination: A Practical Guide", $2^{nd}$ Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Tebben et al., "Three-Dimensional Computerized Reconstruction. Illustration of Incremental Articular Cartilage Thinning," Invest. Radiol. 32(8): 475-484 (1997).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DPGW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).

(56) References Cited

OTHER PUBLICATIONS

Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000) 8:2127.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," Ann Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc. "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 6 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.

(56) References Cited

OTHER PUBLICATIONS

Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10,764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.

(56) References Cited

OTHER PUBLICATIONS

United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
International Searching Authority, International Search Report—International Application No. PCT/US2010/055483, dated Jul. 28, 2011, together with the Written Opinion of the International Searching Authority, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
European Patent Office, European Search Report—Application No. 12170854.9-1526 dated Oct. 9, 2012, 6 pages.
International Searching Authority, International Search Report—International Application No. PCT/US12/59936 dated Jan. 9, 2013, together with the Written Opinion of the International Searching Authority, 11 pages.
European Patent Office, Extended European Search Report—Application No. 10792589.3-2310 dated Feb. 7, 2013, 9 pages.
European Patent Office, European Search Report—Application No. 10192339.9-1257 dated Jan. 23, 2013, 5 pages.
European Patent Office, Extended European Search Report—Application No. 10746859.7-1654 dated Mar. 4, 2013, 7 pages.
European Patent Office, Extended European Search Report—Application No. 12192903.8-1654 dated Apr. 17, 2013, 8 pages.
International Searching Authority, International Search Report—International Application No. PCT/US2012/025280, dated Oct. 25, 2012, together with the Written Opinion of the International Searching Authority, 11 pages.
International Searching Authority, International Search Report—International Application No. PCT/US2009/036165, dated May 7, 2009, together with the Written Opinion of the International Searching Authority, 9 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2012/025277, dated Oct. 25, 2012, together with the Written Opinion of the International Searching Authority, 12 pages.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
International Searching Authority, Great Britain Search and Examination Report—Application No. GB1201112.8 dated Feb. 3, 2014, 4 pages.
International Searching Authority, International Search Report—International Application No. PCT/US2013/035536 dated Jul. 18, 2013, 3 pages.
International Searching Authority, International Search Report—International Application No. PCT/US2013/028762 dated Jun. 21, 2013, 9 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US13/56841 dated Feb. 12, 2014, together with the Written Opinion of the International Searching Authority, 9 pages.
International Searching Authority, International Search Report—International Application No. PCT/US03/39682, dated Oct. 21, 2004, 3 pages.
United States Patent and Trademark Office, Office Action dated Apr. 10, 2008, pertaining to U.S. Appl. No. 10/728,731, 17 pages.
Bromberg & Sunstein LLP, Amendment dated Oct. 7, 2008, pertaining to U.S. Appl. No. 10/728,731, 25 pages.
United States Patent and Trademark Office, Office Action dated Jan. 22, 2009, pertaining to U.S. Appl. No. 10/728,731, 6 pages.
Sunstein Kann Murphy & Timbers LLP, Response to Office Action dated Jan. 22, 2009, pertaining to U.S. Appl. No. 10/728,731, 25 pages.
United States Patent and Trademark Office, Notice of Allowance dated Sep. 21, 2009, pertaining to U.S. Appl. No. 10/728,731, 11 pages.
Moor et al., "Derivation of Final Implant Volume for Breast Reconstruction Using Three Dimensional CT Scan", Eur. J. Plast. Surg., vol. 23, pp. 138-141, 2000.

\* cited by examiner

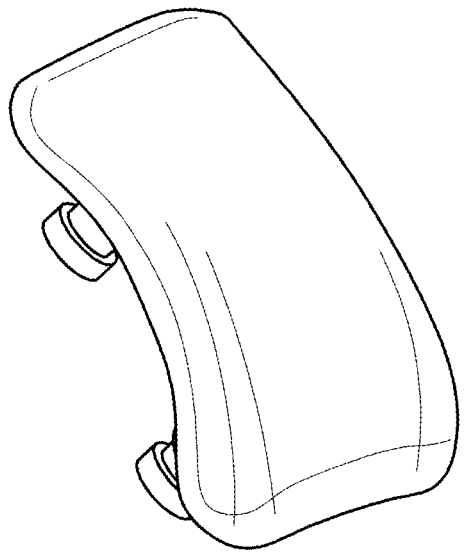 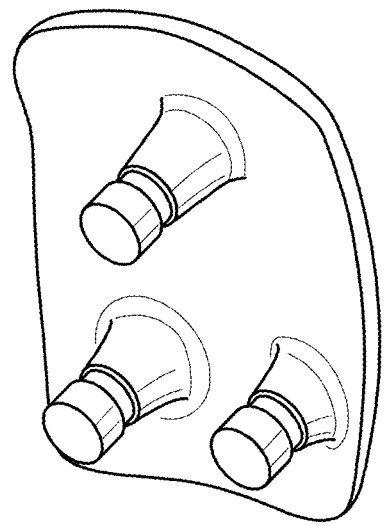
*FIG. 13A*      *FIG. 13B*
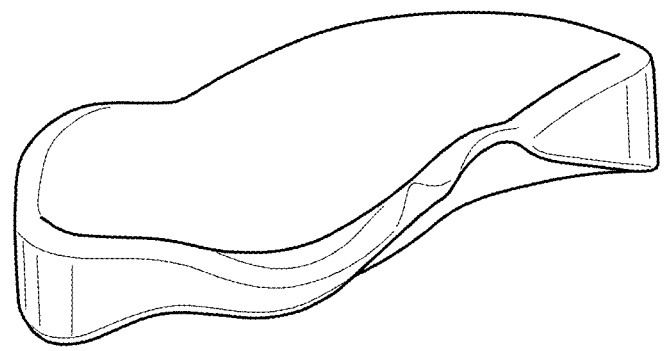
*FIG. 14*

METHODS FOR DETERMINING MENISCAL SIZE AND SHAPE AND FOR DEVISING TREATMENT

CROSS-REFERENCE TO RELATED APPLICATIONS

This application is a continuation of U.S. patent application Ser. No. 13/312,339 filed on Dec. 6, 2011, which in turn is a continuation of U.S. patent application Ser. No. 12/853,599 filed on Aug. 10, 2010 which in turn is a continuation of U.S. patent application Ser. No. 10/704,325 filed on Nov. 7, 2003, which in turn claims priority to U.S. Provisional Patent Application 60/424,964 filed on Nov. 7, 2002.

STATEMENT AS TO RIGHTS TO INVENTIONS MADE UNDER FEDERALLY SPONSORED RESEARCH AND DEVELOPMENT

Certain aspects of the invention described below were made with United States Government support under Advanced Technology Program 70NANBOH3016 awarded by the National Institute of Standards and Technology (NIST). The United States Government may have rights in certain of these inventions.

FIELD OF THE INVENTION

The present invention relates to methods for determining meniscal size and shape for use in designing therapies for the treatment of various joint diseases. This method is then used to design an implant or articular repair system for use in a joint.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and measures typically less than 5 mm in thickness in human joints, with considerable variation depending on the joint and more particularly the site within the joint. In addition, articular cartilage is aneural, avascular, and alymphatic.

Adult cartilage has a limited ability of repair; thus, damage to cartilage produced by disease, such as rheumatoid arthritis and/or osteoarthritis, or trauma can lead to serious physical deformity and debilitation. Furthermore, as human articular cartilage ages, its tensile properties change. Thus, the tensile stiffness and strength of adult cartilage decreases markedly over time as a result of the aging process.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. The use of matrices, tissue scaffolds or other carriers implanted with cells (e.g., chondrocytes, chondrocyte progenitors, stromal cells, mesenchymal stem cells, etc.) has been described as a potential treatment for cartilage and meniscal repair or replacement. See, also, International Publications WO 99/51719 to Fofonoff, published Oct. 14, 1999; WO01/91672 to Simon et al., published Dec. 6, 2001; and WO01/17463 to Mannsmann, published Mar. 15, 2001; U.S. Pat. No. 6,283,980 B1 to Vibe-Hansen et al., issued Sep. 4, 2001, U.S. Pat. No. 5,842,477 to Naughton issued Dec. 1, 1998, U.S. Pat. No. 5,769,899 to Schwartz et al. issued Jun. 23, 1998, U.S. Pat. No. 4,609,551 to Caplan et al. issued Sep. 2, 1986, U.S. Pat. No. 5,041,138 to Vacanti et al. issued Aug. 29, 1991, U.S. Pat. No. 5,197,985 to Caplan et al. issued Mar. 30, 1993, U.S. Pat. No. 5,226,914 to Caplan et al. issued Jul. 13, 1993, U.S. Pat. No. 6,328,765 to Hardwick et al. issued Dec. 11, 2001, U.S. Pat. No. 6,281,195 to Rueger et al. issued Aug. 28, 2001, and U.S. Pat. No. 4,846,835 to Grande issued Jul. 11, 1989. However, clinical outcomes with biologic replacement materials such as allograft and autograft systems and tissue scaffolds have been uncertain since most of these materials cannot achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g. for cosmetic repairs, or suitable metal alloys. See, e.g., U.S. Pat. No. 6,443,991 B1 to Running issued Sep. 3, 2002, U.S. Pat. No. 6,387,131 B1 to Miehlke et al. issued May 14, 2002; U.S. Pat. No. 6,383,228 to Schmotzer issued May 7, 2002; U.S. Pat. No. 6,344,059 B1 to Krakovits et al. issued Feb. 5, 1002; U.S. Pat. No. 6,203,576 to Afriat et al. issued Mar. 20, 2001; U.S. Pat. No. 6,126,690 to Ateshian et al. issued Oct. 3, 2000; U.S. Pat. No. 6,013,103 to Kaufman et al. issued Jan. 11, 2000. Implantation of these prosthetic devices is usually associated with loss of underlying tissue and bone without recovery of the full function allowed by the original cartilage and, with some devices, serious long-term complications associated with the loss of significant amounts of tissue and bone can include infection, osteolysis and also loosening of the implant.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 15 to 20 years, and in some cases even shorter time periods, the patient can run out of therapeutic options ultimately resulting in a painful, non-functional joint.

U.S. Pat. No. 6,206,927 to Fell, et al., issued Mar. 27, 2001, and U.S. Pat. No. 6,558,421 to Fell, et al., issued May 6, 2003, disclose a surgically implantable knee prosthesis that does not require bone resection. This prosthesis is described as substantially elliptical in shape with one or more straight edges. Accordingly, these devices are not designed to substantially conform to the actual shape (contour) of the remaining cartilage in vivo and/or the underlying bone. Thus, integration of the implant can be extremely difficult due to differences in thickness and curvature between the patient's surrounding cartilage and/or the underlying subchondral bone and the prosthesis.

Interpositional knee devices that are not attached to both the tibia and femur have been described. For example, Platt et al. (1969) "Mould Arthroplasty of the Knee," Journal of Bone and Joint Surgery 51 B(1):76-87, describes a hemi-arthroplasty with a convex undersurface that was not rigidly attached to the tibia.

U.S. Pat. No. 4,502,161 to Wall issued Mar. 5, 1985, describes a prosthetic meniscus constructed from materials such as silicone rubber or Teflon with reinforcing materials of stainless steel or nylon strands. U.S. Pat. No. 4,085,466 to Goodfellow et al. issued Mar. 25, 1978, describes a meniscal component made from plastic materials. Reconstruction of meniscal lesions has also been attempted with carbon-fiber-polyurethane-poly (L-lactide). Leeslag, et al., Biological and Biomechanical Performance of Biomaterials (Christel et al., eds.) Elsevier Science Publishers B.V., Amsterdam. 1986. pp. 347-352. Reconstruction of meniscal lesions is also possible with bioresorbable materials and tissue scaffolds.

However, currently available devices do not always provide ideal alignment with the articular surfaces and the resultant joint congruity. Poor alignment and poor joint congruity can, for example, lead to instability of the joint. In the knee joint, instability typically manifests as a lateral instability of the joint.

Thus, there remains a need for methods that recreate natural or near natural relationships between two articular surfaces of the joint (such as the femoral condyle and the tibial plateau).

SUMMARY OF THE INVENTION

In one aspect, when the meniscus is present in the subject, the invention includes measuring the dimensions and/or shape parameters of the meniscus. Such dimensions and parameters include, for example, but are not limited to, the maximum anterior-posterior distance of the meniscus, the maximum medial-lateral distance of the meniscus, the size or area of the meniscal attachment(s), the maximum length of the anterior horn, the maximum and minimum height of the anterior horn, the maximum and minimum height of the body, the maximum and minimum height of the posterior horn, the maximum height and minimum height of the meniscus, the maximum and minimum width of the anterior horn, the maximum and minimum width of the body, the maximum and minimum width of the posterior horn, meniscal radii and angles at various locations. These measurements can then be used to design therapies for the treatment of joint diseases. These treatments can include, for example, meniscal repair systems, cartilage repair systems, articular repair systems and arthroplasty systems and they can consist of, for example, biologic materials, tissue scaffolds, plastic, metal or metal alloys, or combinations thereof. Therapies can be custom-made, typically utilizing at least one or more of these measurements. Alternatively, a pre-made, "off-the-shelf" component closely matching at least one or more of these measurements can be selected.

In another aspect, the invention includes measuring the dimensions and/or shape parameters of the contralateral meniscus. Such dimensions and parameters include, for example, but are not limited to, the maximum anterior-posterior distance of the meniscus, the maximum medial-lateral distance of the meniscus, the size or area of the meniscal attachment(s), the maximum length of the anterior horn, the maximum length of the body, the maximum length of the posterior horn, the maximum and minimum height of the anterior horn, the maximum and minimum height of the body, the maximum and minimum height of the posterior horn, the maximum height and minimum height of the meniscus, the maximum and minimum width of the anterior horn, the maximum and minimum width of the body, the maximum and minimum width of the posterior horn, meniscal radii, and angles at various locations.

In one embodiment, the meniscus of the opposite compartment can be used to create a mirror image of the meniscus on the diseased side. These measurements can then be used to determine meniscal size and/or shape in designing treatments for the diseased joint. These treatments can include, for example, meniscal repair systems, cartilage repair systems, articular repair systems and arthroplasty systems and they can consist of, for example, biologic materials, tissue scaffolds, plastic, metal or metal alloys or combinations thereof. Therapies can be custom-made, typically utilizing at least one or more of these measurements. Alternatively, a pre-made, "off-the-shelf" component matching or closely matching at least one or more of these measurements can be selected.

In yet another embodiment, the 3D geometry of the meniscus on the affected site can be derived from measurements from neighboring articular surfaces and structures to recreate the shape and size of the diseased meniscus. Such measurements include, for example, but are not limited to, tibial bone dimensions, such as maximum anterior-posterior distance, maximum medial-lateral distance, maximum distance from the tibial spine to the edge, width of the tibial spines, height of the tibial spines, area of tibial plateau occupied by tibial spines, depth of tibial plateau, 2D and 3D shape of tibial plateau; femoral condyle bone dimensions, such as maximum anterior-posterior distance, maximum superior-inferior distance, maximum medial-lateral distance, maximum distance from the trochlea to the medial or lateral edge; width and depth of intercondylar notch, curvature at select regions along the femoral condyle, 2D and 3D shape.

In yet another aspect, when applied to the knee joint the invention includes one or more of the following measurements: (1) tibial bone dimensions, for example, maximum anterior-posterior distance, maximum medial-lateral distance, maximum distance from the tibial spine to the edge, width of the tibial spines, height of the tibial spines, area of tibial plateau occupied by tibial spines, depth of tibial plateau, 2D and 3D shape of tibial plateau; (2) tibial cartilage dimensions, including thickness and shape; (3) femoral condyle bone dimensions, for example, maximum anterior-posterior distance, maximum superior-inferior distance, maximum medial-lateral distance, maximum distance from the trochlea to the medial or lateral edge; width and depth of intercondylar notch, curvature at select regions along the femoral condyle, 2D and 3D shape; and (4) femoral cartilage measurements including thickness and shape. These measurements can then be used to estimate meniscal size and/or shape for the treatment of joint diseases. These treatments can include, for example, meniscal repair systems, cartilage repair systems, articular repair systems and arthroplasty systems and it can consist of, for example, biologic materials, tissue scaffolds, plastic, metal or metal alloys, or combinations thereof. Therapies can be custom-made, typically utilizing at least one or more of these measurements. Alternatively, a pre-made, "off-the-shelf" component closely matching at least one or more of these measurements can be selected.

In a further aspect, meniscal measurements are taken from a reference population possessing normal or near normal menisci. Meniscal measurements can include, but are not limited to, for example, the maximum anterior-posterior distance of the meniscus, the maximum medial-lateral distance of the meniscus, the size or area of the meniscal attachment(s), the maximum length of the anterior horn, the maximum length of the body, the maximum length of the posterior horn, the maximum and minimum height of the anterior horn, the maximum and minimum height of the body, the maximum and minimum height of the posterior horn, the maximum height and minimum height of the meniscus, the maximum and minimum width of the anterior horn, the maximum and minimum width of the body, the maximum and minimum width of the posterior horn, meniscal radii and angles at various locations.

Additional non-meniscal measurements can also be taken using the same reference population and may include one or more of the following:

(1) tibial bone dimensions, for example, maximum anterior-posterior distance, maximum medial-lateral distance, maximum distance from the tibial spine to the edge, width of the tibial spines, height of the tibial spines, area of tibial plateau occupied by tibial spines, depth of tibial plateau, 2D and 3D shape of tibial plateau; (2) tibial cartilage dimensions including thickness and shape; (3) femoral condyle bone dimensions, for example, maximum anterior-posterior distance, maximum superior-inferior distance, maximum medial-lateral distance, maximum distance from the trochlea to the medial or lateral edge, width and depth of the intercondylar notch, curvature at select regions along the femoral condyle, 2D and 3D shape, (4) femoral cartilage measurements including thickness and shape; (5) measuring the patellar bone dimensions; (6) measuring the patellar cartilage dimensions including thickness and shape; and/or (7) measuring the size, length or shape of ligamentous structures such as the cruciate ligaments.

The size and/or shape of the menisci in the reference population can then be correlated to one or more of the additional non-meniscal measurements. Once a correlation is established, the bone and/or cartilage and/or ligamentous dimensions with the highest correlation to meniscal size and/or shape can be used to predict meniscal size and/or shape in designing therapies for persons suffering from joint disease. The data from the reference population is typically stored in a database which can be periodically or continuously updated. Using this information, therapies can be devices which include, for example, meniscal repair systems, cartilage repair systems, articular repair systems and arthroplasty systems and they can consist of, for example, biologic materials, tissue scaffolds, plastic, metal or metal alloys, or combinations thereof. Therapies can be custom-made, typically utilizing at least one or more of these measurements. Alternatively, a pre-made, "off-the-shelf" component closely matching at least one or more of these measurements can be selected. For example, a meniscal repair system can be selected utilizing this information. Alternatively, this information can be utilized in shaping an interpositional arthroplasty system.

BRIEF DESCRIPTION OF THE DRAWINGS

FIGS. 13A and B are views of an implant suitable for use on a condyle of the femur shown from the inferior and superior surface viewpoints, respectively.

FIG. 14 is a view of an implant suitable for a portion of the tibial plateau in the knee.

DETAILED DESCRIPTION OF THE INVENTION

Figure 1A:
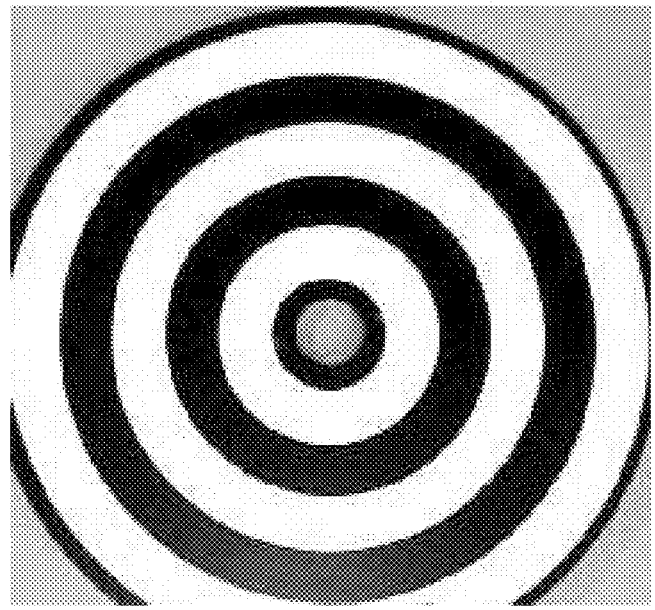
FIG. 1A illustrates an example of a Placido disk of concentrically arranged circles of light.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, the practice of the present invention employs, unless otherwise indicated, conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher.

The present invention solves the need for methods to recreate natural or near natural relationships between two articular surfaces by providing methods for determining meniscal size and shape. Meniscal size and shape can be useful in designing therapies for the treatment of joint diseases including, for example, meniscal repair, meniscal regeneration, and articular repair therapies.

I. Assessment of Joints

The methods and compositions described herein can be used to treat defects resulting from disease of the cartilage (e.g., osteoarthritis), bone damage, cartilage damage, trauma, and/or degeneration due to overuse or age. The invention allows, among other things, a health practitioner to evaluate and treat such defects.

As will be appreciated by those of skill in the art, size, curvature and/or thickness measurements can be obtained using any suitable technique. For example, one dimensional, two dimensional, and/or three dimensional measurements can be obtained using suitable mechanical means, laser devices, electromagnetic or optical tracking systems, molds, materials applied to the articular surface that harden and "memorize the surface contour," and/or one or more imaging techniques known in the art. Measurements can be obtained non-invasively and/or intraoperatively (e.g., using a probe or other surgical device). As will be appreciated by those of skill in the art, the thickness of the repair device can vary at any given point depending upon the depth of the damage to the cartilage and/or bone to be corrected at any particular location on an articular surface.

A. Imaging Techniques

As will be appreciated by those of skill in the art, imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, SPECT, PET, ultrasound imaging techniques, and optical imaging techniques. (See, also, International Patent Publication WO 02/22014 to Alexander, et al., published Mar. 21, 2002; U.S. Pat. No. 6,373,250 to Tsoref et al., issued Apr. 16, 2002; and Vandeberg et al. (2002) *Radiology* 222:430-436). Contrast or other enhancing agents can be employed using any route of administration, e.g. intravenous, intra-articular, etc.

In certain embodiments, CT or MRI is used to assess tissue, bone, cartilage and any defects therein, for example cartilage lesions or areas of diseased cartilage, to obtain information on subchondral bone or cartilage degeneration and to provide morphologic or biochemical or biomechanical information about the area of damage. Specifically, changes such as fissuring, partial or full thickness cartilage loss, and signal changes within residual cartilage can be detected using one or more of these methods. For discussions of the basic NMR principles and techniques, see MRI Basic Principles and Applications, Second Edition, Mark A. Brown and Richard C. Semelka, Wiley-Liss, Inc. (1999). For a discussion of MRI including conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement (RARE) imaging, gradient echo acquisition in the steady state (GRASS), and driven equilibrium Fourier transform (DEFT) imaging, to obtain information on cartilage, see Alexander, et al., WO 02/22014. Thus, in preferred embodiments, the measurements produced are based on three-dimensional images of the joint obtained as described in Alexander, et al., WO 02/22014 or sets of two-dimensional images ultimately yielding 3D information. Two-dimensional and three-dimensional images, or maps, of the cartilage alone or in combination with a movement pattern of the joint, e.g. flexion-extension, translation and/or rotation, can be obtained. Three-dimensional images can include information on movement patterns, contact points, contact zone of two or more opposing articular surfaces, and movement of the contact point or zone during joint motion. Two and three-dimensional images can include information on biochemical composition of the articular cartilage. In addition, imaging techniques can be compared over time, for example to provide up-to-date information on the shape and type of repair material needed.

Any of the imaging devices described herein can also be used intra-operatively (see, also below), for example using a hand-held ultrasound and/or optical probe to image the articular surface intra-operatively.

B. Intraoperative Measurements

Alternatively, or in addition to, non-invasive imaging techniques described above, measurements of the size of an area of diseased cartilage or an area of cartilage loss, measurements of cartilage thickness and/or curvature of cartilage or bone can be obtained intraoperatively during arthroscopy or open arthrotomy. Intraoperative measurements may or may not involve actual contact with one or more areas of the articular surfaces.

Devices suitable for obtaining intraoperative measurements of cartilage or bone or other articular structures, and to generate a topographical map of the surface include but are not limited to, Placido disks and laser interferometers, and/or deformable materials or devices. (See, for example, U.S. Pat. No. 6,382,028 to Wooh et al., issued May 7, 2002; U.S. Pat. No. 6,057,927 to Levesque et al., issued May 2, 2000; U.S. Pat. No. 5,523,843 to Yamane et al. issued Jun. 4, 1996; U.S. Pat. No. 5,847,804 to Sarver et al. issued Dec. 8, 1998; and U.S. Pat. No. 5,684,562 to Fujieda, issued Nov. 4, 1997).

Figure 1B:
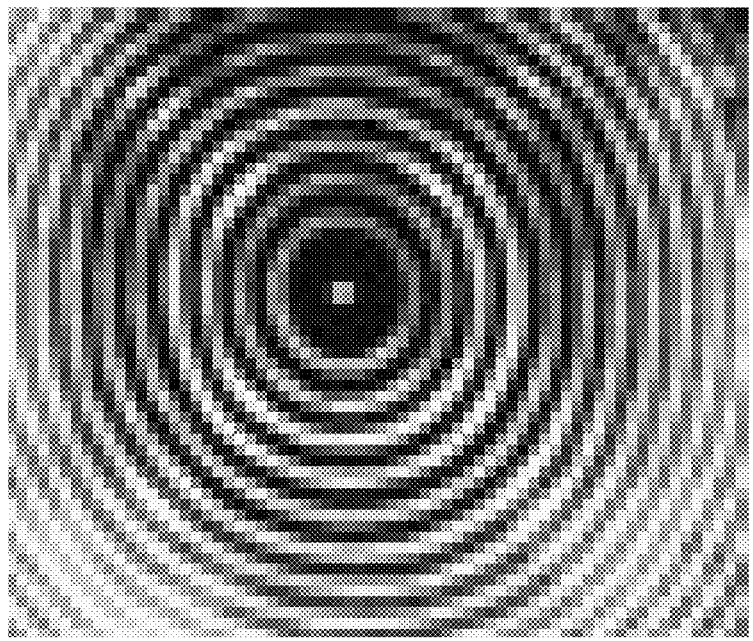
FIG. 1B illustrates an example of a projected Placido disk on a surface of fixed curvature.

FIG. 1A illustrates a Placido disk of concentrically arranged circles of light. The concentric arrays of the Placido disk project well-defined circles of light of varying radii, generated either with laser or white light transported via optical fiber. The Placido disk can be attached to the end of an endoscopic device (or to any probe, for example a hand-held probe) so that the circles of light are projected onto the cartilage surface. FIG. 1B illustrates an example of a Placido disk projected onto the surface of a fixed curvature. One or more imaging cameras can be used (e.g., attached to the device) to capture the reflection of the circles. Mathematical analysis is used to determine the surface curvature. The curvature can then, for example, be visualized on a monitor as a color-coded, topographical map of the cartilage surface. Additionally, a mathematical model of the topographical map can be used to determine the ideal surface topography to replace any cartilage defects in the area analyzed.

Figure 2:
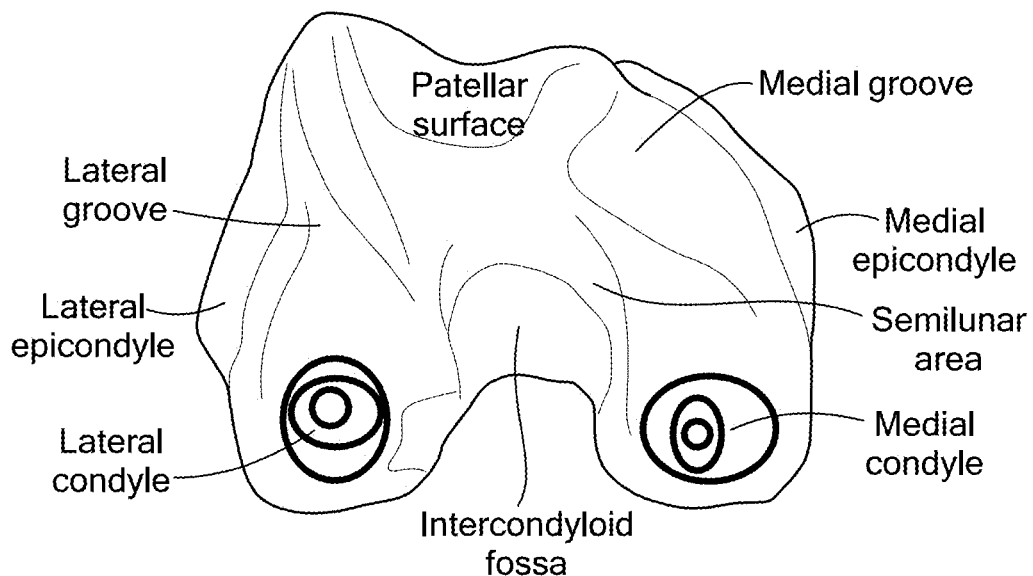
FIG. 2 shows a reflection resulting from a projection of concentric circles of light (Placido Disk) on each femoral condyle, demonstrating the effect of variation in surface contour on the reflected circles.

FIG. 2 shows a reflection resulting from the projection of concentric circles of light (Placido disk) on each femoral condyle, demonstrating the effect of variation in surface contour on reflected circles.

Similarly a laser interferometer can also be attached to the end of an endoscopic device. In addition, a small sensor can be attached to the device in order to determine the cartilage surface or bone curvature using phase shift interferometry, producing a fringe pattern analysis phase map (wave front) visualization of the cartilage surface. The curvature can then be visualized on a monitor as a color coded, topographical map of the cartilage surface. Additionally, a mathematical model of the topographical map can be used to determine the ideal surface topography to replace any cartilage or bone defects in the area analyzed. This computed, ideal surface, or surfaces, can then be visualized on the monitor, and can be used to select the curvature, or curvatures, of the replacement cartilage.

Figure 3:
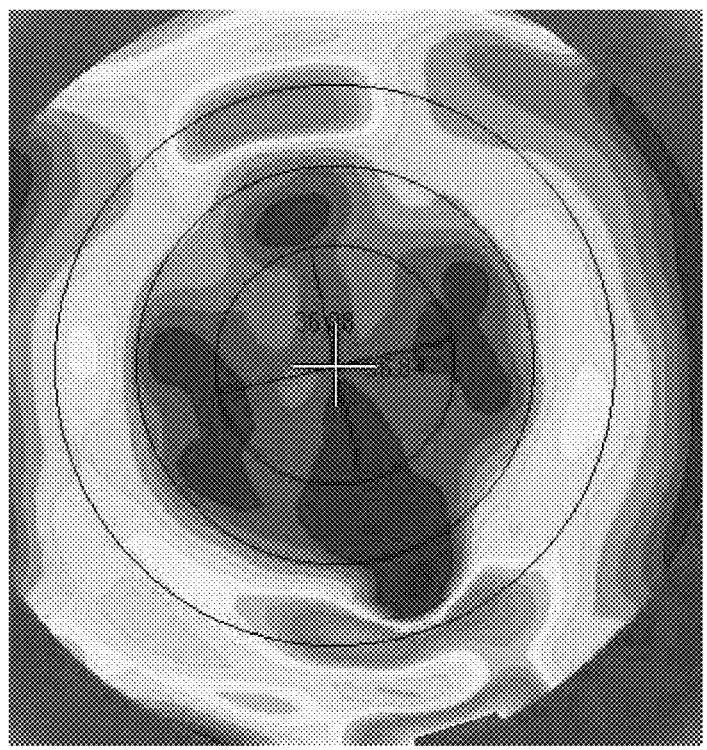
FIG. 3 illustrates an example of a 2D topographical map of an irregularly curved surface.
Figure 4:
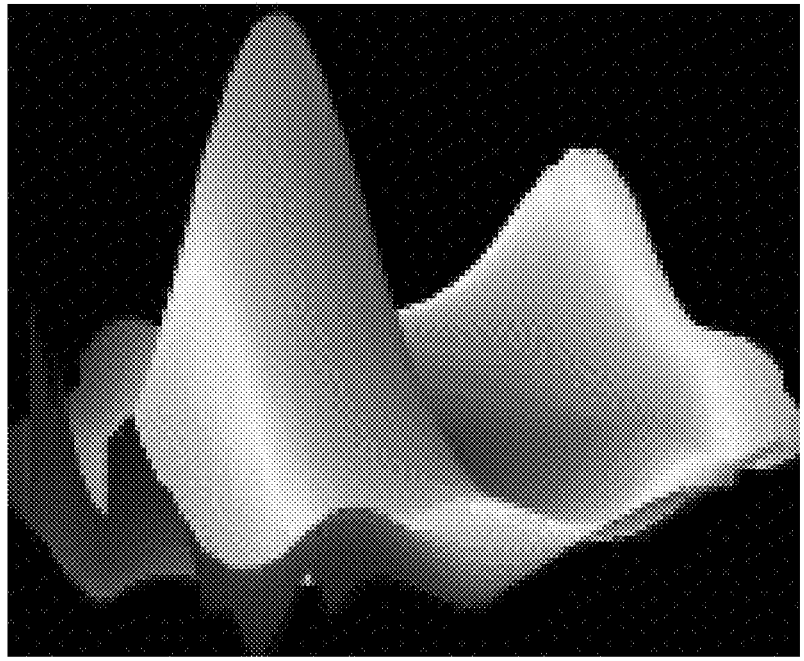
FIG. 4 illustrates an example of a 3D topographical map of an irregularly curved surface.
Figure 5:
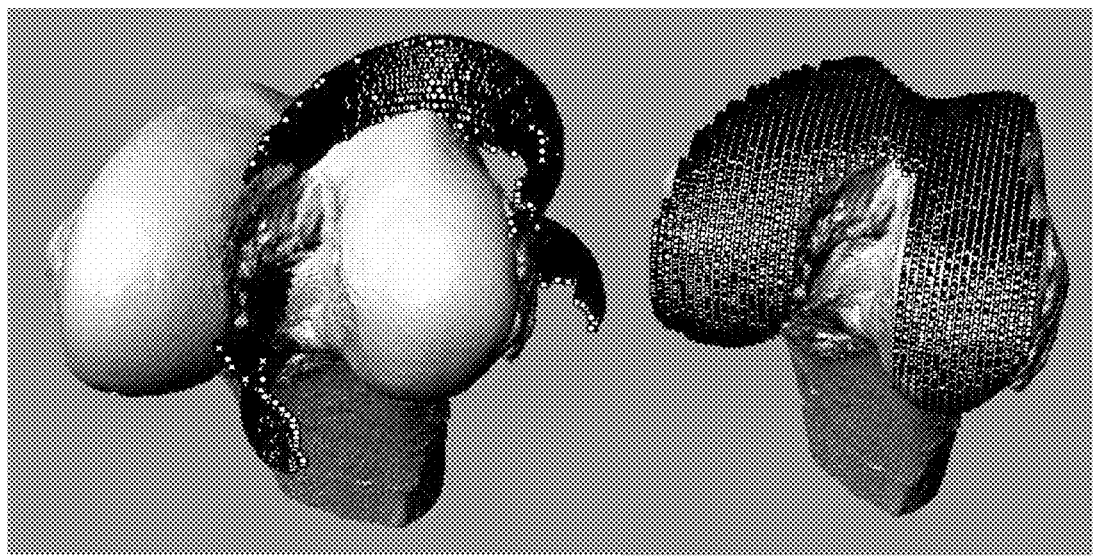
FIG. 5 illustrates surface registration of MRI surface and a digitized surface using a laser scanner. The illustration to the left shows the surface before registration and the illustration to the right shows the surface after registration.

One skilled in the art will readily recognize that other techniques for optical measurements of the cartilage surface curvature can be employed without departing from the scope of the invention. For example, a 2-dimensional or 3-dimensional map, such as that shown in FIG. 3 and FIG. 4 can be generated.

Mechanical devices (e.g., probes) can also be used for intraoperative measurements, for example, deformable materials such as gels, molds, any hardening materials (e.g., materials that remain deformable until they are heated, cooled, or otherwise manipulated). See, e.g., WO 02/34310 to Dickson et al., published May 2, 2002. For example, a deformable gel can be applied to a femoral condyle. The side of the gel pointing towards the condyle can yield a negative impression of the surface contour of the condyle. The negative impression can then be used to determine the size of a defect, the depth of a defect and the curvature of the articular surface in and adjacent to a defect. This information can be used to select a therapy, e.g. an articular surface repair system. In another example, a hardening material can be applied to an articular surface, e.g. a femoral condyle or a tibial plateau. The hardening material can remain on the articular surface until hardening has occurred. The hardening material can then be removed from the articular surface. The side of the hardening material pointing towards the articular surface can yield a negative impression of the articular surface. The negative impression can then be used to determine the size of a defect, the depth of a defect and the curvature of the articular surface in and adjacent to a defect. This information can then be used to select a therapy, e.g. an articular surface repair system. In some embodiments, the hardening system can remain in place and form the actual articular surface repair system.

In certain embodiments, the deformable material comprises a plurality of individually moveable mechanical elements. When pressed against the surface of interest, each element can be pushed in the opposing direction and the extent to which it is pushed (deformed) can correspond to the curvature of the surface of interest. The device can include a brake mechanism so that the elements are maintained in the position that conforms to the surface of the cartilage and/or bone. The device can then be removed from the patient and analyzed for curvature. Alternatively, each individual moveable element can include markers indicating the amount and/or degree it is deformed at a given spot. A camera can be used to intra-operatively image the device and the image can be saved and analyzed for curvature information. Suitable markers include, but are not limited to, actual linear measurements (metric or empirical), different colors corresponding to different amounts of deformation and/or different shades or hues of the same color(s). Displacement of the moveable elements can also be measured using electronic means.

Other devices to measure cartilage and subchondral bone intraoperatively include, for example, ultrasound probes. An ultrasound probe, preferably handheld, can be applied to the cartilage and the curvature of the cartilage and/or the subchondral bone can be measured. Moreover, the size of a cartilage defect can be assessed and the thickness of the articular cartilage can be determined. Such ultrasound measurements can be obtained in A-mode, B-mode, or C-mode. If A-mode measurements are obtained, an operator can typically repeat the measurements with several different probe orientations, e.g. mediolateral and anteroposterior, in order to derive a three-dimensional assessment of size, curvature and thickness.

One skilled in the art will easily recognize that different probe designs are possible using the optical, laser interferometry, mechanical and ultrasound probes. The probes are preferably handheld. In certain embodiments, the probes or at least a portion of the probe, typically the portion that is in contact with the tissue, can be sterile. Sterility can be achieved with use of sterile covers, for example similar to those disclosed in WO 99/08598A1 to Lang, published Feb. 25, 1999.

Analysis on the curvature of the articular cartilage or subchondral bone using imaging tests and/or intraoperative measurements can be used to determine the size of an area of diseased cartilage or cartilage loss. For example, the curvature can change abruptly in areas of cartilage loss. Such abrupt or sudden changes in curvature can be used to detect the boundaries of diseased cartilage or cartilage defects.

II. Segmentation of Articular Cartilage, Bone and Menisci

A semi-automated segmentation approach has been implemented based on the live wire algorithm, which provides a high degree of flexibility and therefore holds the potential to improve segmentation of osteoarthritic cartilage considerably. Images are optionally pre-processed using a non-linear diffusion filter. The live wire algorithm assigns a list of features to each oriented edge between two pixels (boundary element-bel) in an image. Using an individual cost function for each feature, the feature values are converted into cost values. The costs for each feature are added up by means of a predetermined weighting scheme, resulting in a single joint cost value between 0 and 1 for each bel b that expresses the likelihood of b being part of the cartilage boundary. To determine the contour of a cartilage object, the operator chooses a starting pixel P. Subsequently, the system calculates the least cost bel path from each image pixel to P with a dynamic programming scheme. When the operator selects another pixel, the system displays the calculated path from the current mouse position to P in real time. This current path can be frozen as part of the cartilage contour by the operator. This way, the operator has to assemble the desired contour in each slice from a number of pieces ("strokes").

The features of a bel b used with this segmentation technique are the gray values left and right of b and the magnitude of the gray level gradient across b.

As will be appreciated by those of skill in the art, all or a portion of the segmentation processes described can be automated as desired. As will be appreciated by those of skill in the art, other segmentation techniques including but not limited to thresholding, grey level gradient techniques, snakes, model based segmentation, watershed, clustering, statistical segmentation, filtering including linear diffusion filtering can be employed.

III. Validation of Cartilage Surface Segmentation

In order to validate the accuracy of the segmentation technique for the articular cartilage surface, the cartilage surface extracted from MRI scans can be compared with results obtained from segmentation of the joint surface data which is acquired, for example, using a laser scanner after specimen dissection. The resulting two surfaces from MRI and laser scan can be registered using the iterative closest point method, and the distance between each point on the MRI surface to the registered laser scan surface can be used to determine the accuracy of the MRI segmentation results. FIG.

5 shows the MRI and digitized surfaces before and after registration. The distance measurements for the two specimens are shown in TABLE 1.

TABLE 1

DISTANCE CALCULATIONS BETWEEN SEGMENTED MRI AND LASER DIGITIZED SURFACES (IN MM)

| Specimen | Minimum Distance | Maximum Distance | Mean Distance M | Standard Deviation $\sigma$ |
|---|---|---|---|---|
| 1 | 3.60447e−05 | 2.10894 | 0.325663 | 0.312803 |
| 2 | 2.79092e−06 | 1.616828 | 0.262131 | 0.234424 |

In this example, the data illustrate that the average error between the segmented MRI surface and the laser scan surface is within the range of the resolution of the MRI scan. Thus, the segmentation approach yields an accuracy within the given MRI scan parameters.

IV. Calculation and Visualization OF Cartilage Thickness Distribution

A suitable approach for calculating the cartilage thickness is based on a 3D Euclidean distance transform (EDT). An algorithm by Saito and Toriwaki can be used to achieve computationally very fast (less than 10 sec for a 256×256×60 data set on a SGI O2) data processing. The algorithm functions by decomposing the calculation into a series of 3 one-dimensional transformations and uses the square of the actual distances. This process accelerates the analysis by avoiding the determination of square roots. For initialization, voxels on the inner cartilage surface (ICS) are given a value of 0, whereas all other voxels, including the ones on the outer cartilage surface (OCS) are set to 1.

First, for a binary input picture $F=\{f_{ijk}\}$ ($1 \leq i \leq L$, $1 \leq j \leq M$, $1 \leq k \leq N$) a new picture $G=\{g_{ijk}\}$ is derived using equation 1 ($\alpha$, $\beta$, and $\gamma$ denote the voxel dimensions).

$$g_{ijk} = \min_x\{(\alpha(i-x))^2; f_{xjk}=0; 1 \leq x \leq L\} \quad [\text{Eq. 1}]$$

Thus, each point is assigned the square of the distance to the closest feature point in the same row in i-direction. Second, G is converted into $H=\{h_{ijk}\}$ using equation 2.

$$h_{ijk} = \min_y\{g_{iyk}(\beta(j-y))^2; 1 \leq y \leq M\} \quad [\text{Eq. 2}]$$

The algorithm searches each column in j-direction. According to the Pythagorean theorem, the sum of the square distance between a point (i,j,k) and a point (i,y,k) in the same column, $(\beta(j-y))^2$, and the square distance between (i,y,k) and a particular feature point, $g_{iyk}$, equals the square distance between the point (i,j,k) and that feature point. The minimum of these sums is the square distance between (i,j,k) and the closest feature point in the two-dimensional i-j-plane.

The third dimension is added by equation 3, which is the same transformation as described in equation 2 for the k-direction.

$$s_{ijk} = \min_z\{h_{ijz}+(\gamma(k-z))^2; 1 \leq z \leq N\} \quad [\text{Eq. 3}]$$

Figure 6:
FIG. 6 is a reproduction of a three-dimensional thickness map of the articular cartilage of the distal femur. Three-dimensional thickness maps can be generated, for example, from ultrasound, CT or MRI data. Dark holes within the substances of the cartilage indicate areas of full thickness cartilage loss.

After completion of the EDT, the thickness of the cartilage for a given point (a,b,c) on the OCS equals the square root of $s_{abc}$. This results in a truly three-dimensional distance value determined normal to the ICS. The x, y, and z position of each pixel located along the bone-cartilage interface is registered on a 3D map and thickness values are translated into color values. In this fashion, the anatomic location of each pixel at the bone-cartilage interface can be displayed simultaneously with the thickness of the cartilage for that given location (FIG. 6).

As will be appreciated by those of skill in the art, other techniques for calculating cartilage thickness can be applied, for example using the LaPlace equation, without departing from the scope of the invention.

V. Calculation and Visualization of Cartilage Curvature Distribution

Another relevant parameter for the analysis of articular cartilage surfaces is curvature. In a fashion similar to the thickness map, a set of curvature maps can be derived from the cartilage surface data that is extracted from the MRI.

A local bi-cubic surface patch is fitted to the cartilage surface based on a sub-sampling scheme in which every other surface point is used to generate a mesh of 5×5 point elements. Thus, before performing the fit the density of the data is reduced in order to smooth the fitted surface and to reduce the computational complexity.

After computation of the local bi-cubic surface fits, the unit normal vectors $\{n\}$ are implicitly estimated from the surface fit data. The corresponding curvature and its orientation are then given by:

$$K_i = \arccos(n_0 \cdot n_i)/ds_i = d\theta/ds_i,$$

where $n_o$ is the unit normal vector at the point (u, v) where the curvature is being estimated and $n_i$ (i=1, . . . , 24) are the unit normal vectors at each one of the surrounding points in the 5×5 local surface patch. FIG. 6 shows an example of the maximum principal curvature maps (value and direction), estimated using the bi-cubic surface patch fitting approach.

As will be appreciated by those of skill in the art, other techniques, such as n-degree polynomial surface interpolation or approximation, parametric surface interpolation or approximation and different discrete curvature estimation methods for measuring curvature or 3D shape can be applied.

VI. Fusion of Image Data from Multiple Planes

Recently, technology enabling the acquisition of isotropic or near-isotropic 3-dimensional image data has been developed. However, most MRI scans are still acquired with a slice thickness that is 3 or more times greater than the in-plane resolution. This leads to limitations with respect to 3D image analysis and visualization. The structure of 3-dimensional objects cannot be described with the same accuracy in all three dimensions. Partial volume effects hinder interpretation and measurements in the z-dimension to a greater extent than in the x-y plane.

To address the problems associated with non-isotropic image resolutions, one or more first scans S1 are taken in a first plane. Each of the first scans are parallel to each other. Thereafter, one or more second scans S2 are taken with an imaging plane oriented to the first scan S1 so that the planes intersect. For example, scans S1 can be in a first plane while scans S2 are in a plane perpendicular to the first plane. Additional scans in other planes or directions, e.g., S3, S4. Sn, can also be obtained in addition to the perpendicular scans or instead of the perpendicular scans. S2, and any other scans, can have the same in-plane resolution as S1. Any or all of the scans can also contain a sufficient number of slices to cover the entire field of view of S1. In this scenario, two data volumes with information from the same 3D space or overlapping 3D spaces can be generated.

Data can be merged from these two scans to extract the objects of interest in each scan independently. Further, a subsequent analysis can combine these two segmented data sets in one coordinate system, as is shown in FIG. 6. This technique is helpful in outlining the boundaries of objects that are oriented parallel to the imaging plane of S1, but therefore will be perpendicular to the imaging plane of S2.

Figure 7:
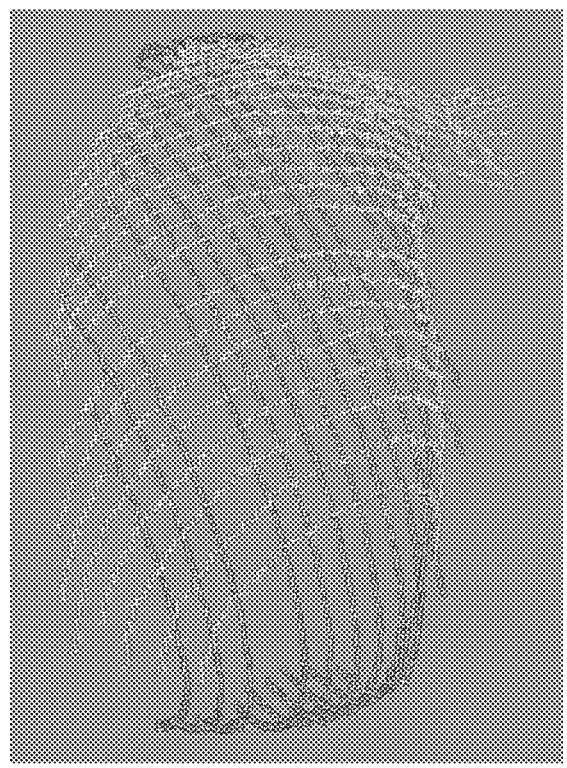
FIG. 7 illustrates the cartilage surface of a medial femoral condyle from a sagittal scan (blue) and a coronal scan (red).

For quantitative measurements, such as determining the cartilage volume, it can be advantageous to combine S1 and S2 directly into a third data volume. This third data volume is typically isotropic or near-isotropic with a resolution corresponding to the in-plane resolution of S1 and S2, thus reducing partial volume effects between slices (FIG. 7). S1 and S2 can first be registered into the same coordinate system. If both scans are acquired during the same session (without moving the patient between scans), the image header information is used to obtain the transformation matrix. Otherwise, a mutual information-based rigid registration is applied. The gray value for each voxel V of the third data volume is calculated as follows:

(1) determine the position in 3D space for V;
(2) determine the gray values in S1 and S2 at this position;
(3) interpolate the two gray values into a single gray value G; and
(4) assign G to V.

As an alternative to fusion of two or more imaging planes, data can be obtained with isotropic or near isotropic resolution. This is possible, for example, with spiral CT acquisition technique or novel MRI pulse sequence such as 3D acquisition techniques. Such 3D acquisition techniques include 3D Driven Equilibrium Transfer (DEFT), 3D Fast Spin-Echo (FSE), 3D SSFP (Steady State Free Precession), 3D Gradient Echo (GRE), 3D Spoiled Gradient Echo (SPGR), and 3D Flexible Equilibrium MR (FEMR) techniques. Images can be obtained using fat saturation or using water selective excitation. Typically, an isotropic resolution of 0.5×0.5×0.5 mm or less is desirable, although in select circumstances 1.0×1.0× 1.0 and even larger can yield adequate results. With near isotropic resolution, the variation in voxel dimensions in one or more planes does not usually exceed 50%.

VII. In Vivo Measurement of Meniscal Dimensions

The dimensions and shape of a personalized interpositional arthroplasty system can be determined by measuring a patient's meniscal shape and size and by evaluating the 3D geometry of the articular cartilage. Many osteoarthritis patients, however, have torn menisci, often times with only small or no meniscal remnants. In these patients, the shape of a personalized interpositional arthroplasty system can be determined by acquiring measurements of surrounding articular surfaces and structures.

In the knee, for example, a few measurements can be made on the femoral and tibial bone in MR images of the diseased knee. For optimal fit, the shape of the superior surface of the implant should resemble that of the superior surface of the respective meniscus. Measurements of the bones can help determine how well meniscal dimensions can be predicted.

Figure 8A:
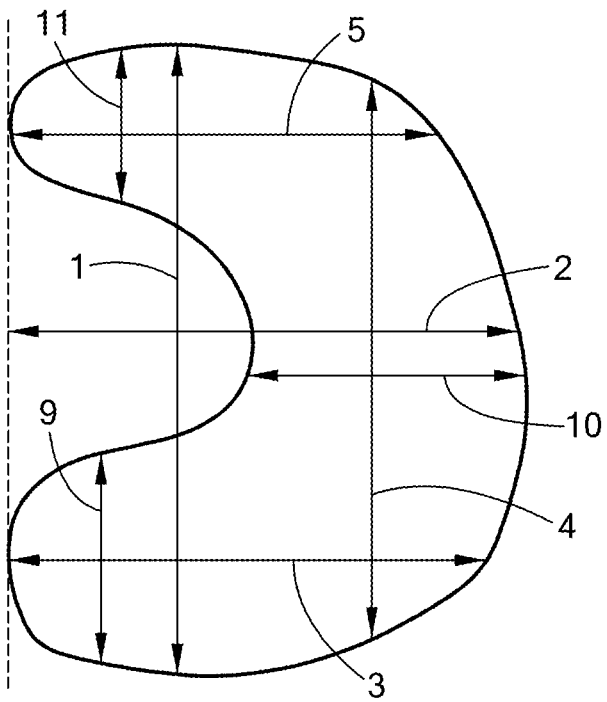
FIG. 8A illustrates an axial view of a meniscus.
Figure 8B:
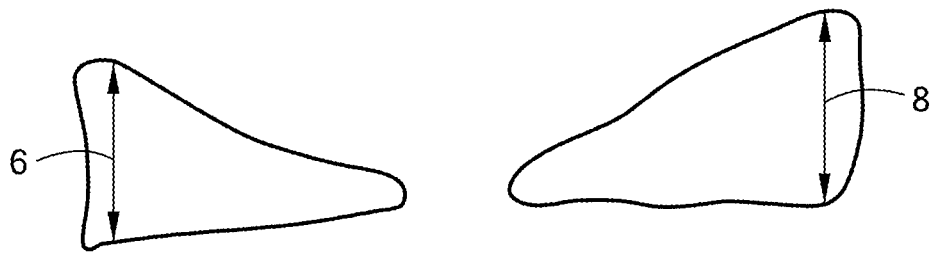
FIG. 8B illustrates a sagittal view of the meniscus.
Figure 8C:
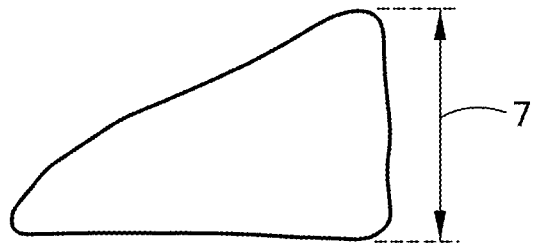
FIG. 8C illustrates a coronal view of the meniscus.

FIG. 8A illustrates an axial view of a meniscus 100. The meniscus has a maximum anterior-posterior distance 1, and a maximum medial lateral distance 2. In the knee, the meniscus compensates for an anterior horn and a posterior which each have a maximum length 3, 5 and width 9, 11. The body itself has a maximum length 4 and width 10 which are a function of the patient's anatomy. FIG. 8B illustrates a sagittal view of the meniscus in FIG. 8A. The meniscus 100 has a maximum height 6, 8 which correlates to the maximum height of the anterior horn and the posterior horn. FIG. 8C illustrates a coronal view of the meniscus 100. From the coronal view it is apparent that the body has a maximum and minimum height.

Figure 9A:
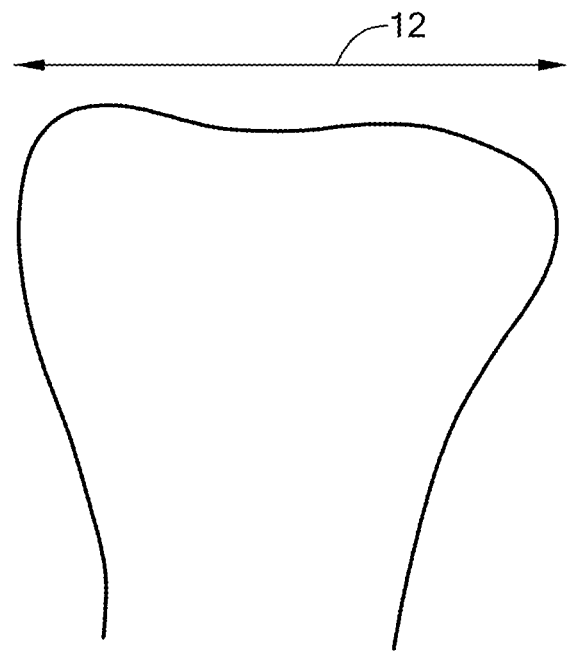
FIG. 9A illustrates a sagittal view of the tibia.
Figure 9B:
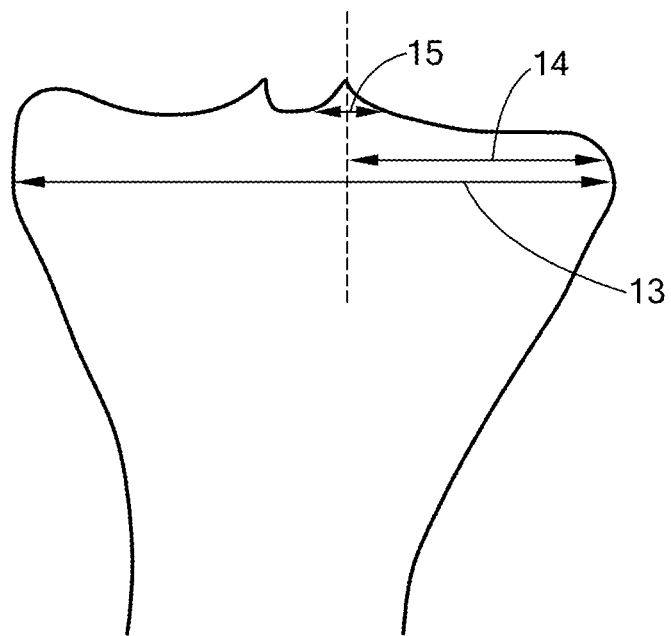
FIG. 9B illustrates a coronal view of the tibia.

Turning now to FIG. 9A, a sagittal view of a tibia 110 is shown. The tibia has a maximum anterior-posterior distance 12. FIG. 9B illustrates the coronal view of the tibia 110 shown in FIG. 9A. From the sagittal view it is apparent that the tibia has a maximum medial-lateral distance 13, a maximum distance from the tibial spine to the edge 14, and a width 15.

Figure 10A:
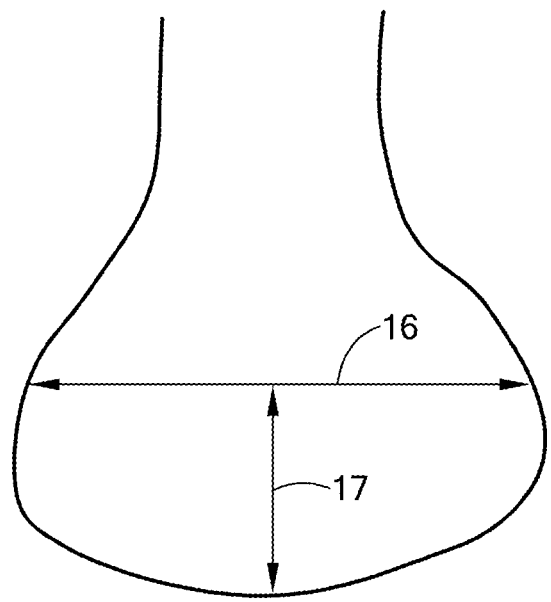
FIG. 10A illustrates a sagittal view of the femur.
Figure 10B:
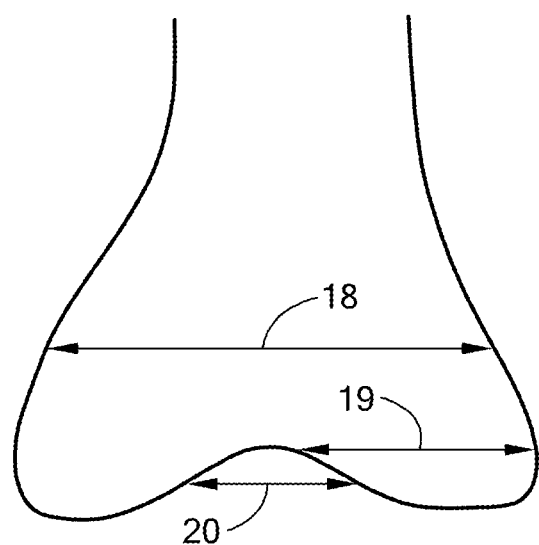
FIG. 10B illustrates a coronal view of the femur.

The tibia mates with the femur 120, which is shown in a sagittal view in FIG. 10A. The femur has a maximum anterior-posterior distance 16 and a maximum superior-interior distance 17. From the coronal view shown in FIG. 10B the maximum medial-lateral distance 18, the distance from the trochlea to the edge 19, and the width of the intercondylar notch 20 is apparent.

A Pearson's correlation coefficient r can be obtained for a variety of measurements to assess how well one variable is expressed by another variable. Suitable measurements include, for example, the following measurements:

antero-posterior (AP) length of medial (lateral) meniscus with AP length of medial (lateral) femoral condyle;

AP length of medial (lateral) meniscus with AP length of medial (lateral) tibial plateau;

medio-lateral (ML) width of medial (lateral) meniscus with ML width of medial (lateral) femoral condyle;

ML width of medial (lateral) meniscus with ML width of medial (lateral) tibial plateau;

Y coordinate of highest point of medial (lateral) meniscus with y coordinate of highest point of medial (lateral) tibial spine;

X coordinate of medial (lateral) margin of medial (lateral) meniscus with x coordinate of medial (lateral) margin of medial (lateral) femoral condyle; and X coordinate of medial (lateral) margin of medial (lateral) meniscus with x coordinate of medial (lateral) margin of medial (lateral) tibial plateau.

Examples of measurements obtained are summarized in TABLE 2.

TABLE 2

CORRELATION BETWEEN MENISCAL DIMENSIONS AND DIMENSIONS OF FEMORAL AND TIBIAL BONE

| Measurement | Imaging Plane | N | Pearson's r |
|---|---|---|---|
| AP Length: medial meniscus-medial femoral condyle | Sagittal | 23 | 0.74 |
| AP Length: lateral meniscus-lateral femoral condyle | Sagittal | 24 | 0.73 |
| AP Length: medial meniscus-medial tibial plateau | Sagittal | 23 | 0.79 |
| AP Length: lateral meniscus-lateral tibial plateau | Sagittal | 24 | 0.27 |
| ML Width: menisci-femur | Coronal | 12 | 0.91 |
| ML Width: menisci-tibia | Coronal | 12 | 0.92 |
| ML Width: menisci-medial femoral condyle | Coronal | 12 | 0.81 |
| ML Width: menisci-lateral femoral condyle | Coronal | 12 | 0.65 |
| ML Width: menisci-medial tibial plateau | Coronal | 12 | 0.86 |
| ML Width: menisci-lateral tibial plateau | Coronal | 12 | 0.48 |
| ML Width: medial meniscus-medial femoral condyle | Coronal | 12 | 0.95 |
| ML Width: lateral meniscus-lateral femoral condyle | Coronal | 12 | 0.45 |
| ML Width: medial meniscus-medial tibial plateau | Coronal | 12 | 0.69 |
| ML Width: lateral meniscus-lateral tibial plateau | Coronal | 12 | 0.34 |
| ML Length: medial meniscus-lateral meniscus | Coronal | 12 | 0.12 |
| Meniscal Height: medial meniscus-lateral meniscus | Coronal | 12 | 0.01 |
| Meniscal Height: Medial meniscal height-medial femoral height | Coronal | 12 | 0.22 |
| Meniscal Height: Lateral meniscal height-lateral femoral height | Coronal | 12 | 0.22 |
| Meniscal Height: Medial meniscal height-medial tibial height | Coronal | 12 | 0.55 |
| Meniscal Height: Lateral meniscal height-lateral tibial height | Coronal | 12 | 0.17 |
| Highest Point (y coordinate): medial meniscus-medial tibial spine | Coronal | 12 | 0.99 |

TABLE 2-continued

CORRELATION BETWEEN MENISCAL DIMENSIONS
AND DIMENSIONS OF FEMORAL AND TIBIAL BONE

| Measurement | Imaging Plane | N | Pearson's r |
|---|---|---|---|
| Highest Point (y coordinate): lateral meniscus-lateral tibial spine | Coronal | 12 | 0.90 |
| Medial margin (x-coordinate): medial meniscus-femoral condyle | Coronal | 12 | 1.00 |
| Lateral margin (x-coordinate): lateral meniscus-lateral femoral condyle | Coronal | 12 | 1.00 |
| Medial Margin (x-coordinate): medial meniscus-medial tibial plateau | Coronal | 12 | 1.00 |
| Lateral Margin (x-coordinate): lateral meniscus-lateral tibial plateau | Coronal | 12 | 1.00 |

The Pearsons' coefficient determines the relationship between two sizes that are measured. The higher the correlation, the better the relationship between two measurements. From the data in TABLE 2, it becomes evident that, in the knee, the AP length of both medial and lateral menisci can be predicted well by measuring the length of the respective femoral condyle. For the medial meniscus, the length of the medial tibial plateau can also be used. The ML width of the medial femoral condyle is a good predictor for the width of the medial meniscus. The height of the medial and lateral tibial spines correlates well with the height of the respective menisci. Correlations between ML width of the lateral meniscus and width of the lateral femoral condyle and tibial spine are lower due to a high variability of the most lateral point of the lateral meniscus. As opposed to these outermost points of the lateral meniscus, the main margins correlate very well with the margins of the tibia and femur. This is also the case for the medial meniscus. Consequently, the outer margins of medial and lateral menisci can be determined.

These results show that meniscal dimensions can be predicted in a reliable fashion by measuring bony landmarks in MR images. Where the Pearson's coefficient is high (e.g., close to 1), the two measurements can, in effect, be used interchangeably to represent the measurement desired. Where the Pearson's coefficient is low (e.g., 0.34), a correction factor may be applied to the measurement. The measurement as corrected may then equal or approximate the corresponding measurement. In some instances, use of a correction factor may not be feasible or desired. In that instance, other approaches, such as logistic regression and multivariate analysis, can be used as an alternative without departing from the scope of the invention.

A person of skill in the art will appreciate that while this data has been presented with respect to the meniscus in the knee and measurement of knee anatomy relative thereto, similar results would occur in other joints within a body as well. Further, it is anticipated that a library of measurements can be created, for example for generating one or more correlation factors that can be used for a particular joint. For example, a single correlation factor can be generated using a plurality of measurements on different subjects.

Alternatively, a plurality of correlation factors can be generated based on, for example, joint assessed, size, weight, body mass index, age, sex of a patient, ethnic background. In this scenario, a patient seeking treatment can be assessed. Measurements can be taken of, for example, the medial femoral condyle. The correlation factor for the medial femoral condyle in the patient can then be compared to a correlation factor calculated based on samples wherein the sample patients had the same, or were within a defined range for factors, including for example: size, weight, age and sex.

VIII. Surface Digitization

Digitized surface data from menisci of cadaveric specimens for generation of a generic meniscal model can be acquired using a Titanium FaroArm® coordinate measurement machine (CMM) (FARO Technologies Inc., Lake Mary, Fla.).

IX. 3D Design Techniques for Anatomically Correct Interpositional Arthroplasty System The design workflow for each implant can consist of a combination of one or more of the following steps:

a. Fusion of the sagittal and coronal 3D SPGR or 2D or 3D FSE data or other sequences for a joint;
b. Segmentation of point data from the cartilage surface of a joint;
c. Fusion of the sagittal and coronal 2D or 3D FSE or 2D SE data or other sequences of a joint;
d. Segmentation point data of the superior meniscal surface;
e. Combination of cartilage surface data and meniscal surface data to serve as model for a surface of an implant;
f. Compression of a meniscal surface by factor ranging from 0.2 to 0.99;
g. Conversion of point cloud data for a superior and an inferior implant surface into parametric surface data; and
h. Cutting of parametric surface data sets to determine exact shape of implant.

In many patients with advanced osteoarthritis, however, the meniscus is, to a great extent, depleted, and therefore cannot serve directly as a template from which the superior implant surface can be derived. In these cases, dimensions of the remaining joint bone, can be used to adjust the size of a generic meniscal model, which can then serve as a template for the implant.

X. Derivation of Implant Surfaces from Cartilage and Healthy Meniscal Surfaces

Figure 11A:
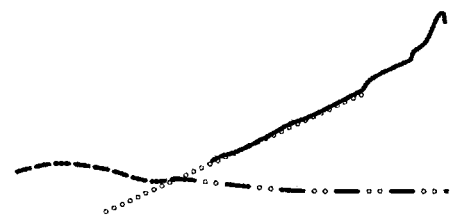
FIGS. 11A-C illustrate a chart showing the tibial cartilage surface and superior meniscal surface combined after extraction from a coronal FSE, and a meniscal surface scaled to account for compression under loading conditions. From the information is derived the cross-section of the implant, FIG. 11C.
Figure 11B:
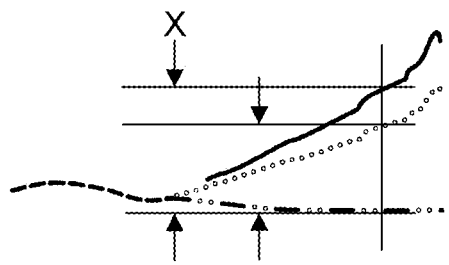
Figure 11C:
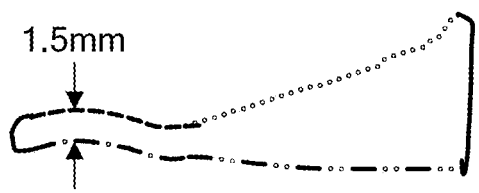

The superior surface of an implant can be modeled based on the superior meniscal surface and the joint cartilage surface in those areas that are not covered by the meniscus. Therefore, after the slice-by-slice segmentation of the superior meniscal surface from the SE or FSE or other MRI images and the tibial cartilage surface from the 3D SPGR or FSE or other MRI images, both data sets will be combined (FIGS. 11A-C). To determine the composite surface for the prosthesis, the intersection between the two surfaces is located. In the event that the two surfaces do not intersect in a particular slice, the intersection between the tangential line through the d. Segmentation point data of the superior meniscal surface;
e. Combination of cartilage surface data and meniscal surface data to serve as model for a surface of an implant;
f. Compression of a meniscal surface by factor ranging from 0.2 to 0.99;
g. Conversion of point cloud data for a superior and an inferior implant surface into parametric surface data; and
h. Cutting of parametric surface data sets to determine exact shape of implant.

In many patients with advanced osteoarthritis, however, the meniscus is, to a great extent, depleted, and therefore cannot serve directly as a template from which the superior implant surface can be derived. In these cases, dimensions of the remaining joint bone, can be used to adjust the size of a generic meniscal model, which can then serve as a template for the implant.

X. Derivation of Implant Surfaces from Cartilage and Healthy Meniscal Surfaces

The superior surface of an implant can be modeled based on the superior meniscal surface and the joint cartilage surface in those areas that are not covered by the meniscus. Therefore, after the slice-by-slice segmentation of the superior meniscal surface from the SE or FSE or other MRI images and the tibial cartilage surface from the 3D SPGR or FSE or other MRI images, both data sets will be combined (FIGS. 11A-C). To determine the composite surface for the prosthesis, the intersection between the two surfaces is located. In the event that the two surfaces do not intersect in a particular slice, the intersection between the tangential line through the central end of the meniscal surface with the tibial surface will be calculated (FIG. 11A). To account for natural compression of the elastic meniscus under load, its height can be adjusted, for example, to 60% of the original height (FIG. 11B). For this purpose, each point on the meniscal surface is connected to the closest point on the cartilage surface. The new point for the adjusted meniscal surface is chosen at 60% of the distance from the tibial cartilage surface.

As will be appreciated by those of skill in the art, a variety of other adjustment ratios can be used without departing from the scope of the invention. Suitable adjustment ratios will vary depending on patient physiology and desired degree of correction and include, for example, ratios that range from 0.2 to 1.5. The amount of height adjustment of the implant relative to the natural meniscus will vary depending upon the material that the implant is manufactured from. For example, where the implant is manufactured from a material having a high degree of elasticity, it may be desirable to use an adjustment greater than 1. Where the material has a low degree of elasticity, the adjustment is likely to approach 50%. The appropriate adjustment will also depend upon the joint for which the implant is manufactured. Thus, for example, an implant manufactured for the knee using a material with a low degree of elasticity can have an adjustment of between 50-70%, while an implant manufactured for the shoulder also using a material with a low degree of elasticity may have a desired adjustment of 60-80%. Persons of skill in the art will appreciate that the correction factor for an implant will vary depending upon the target joint and the properties of the material from which the implant is manufactured.

The adjustment ratio can also vary depending on the location within a joint with a plurality of ratios possible for any given design. For example, in a knee joint, an adjustment ratio close to 0.8 can be used anteriorly, while an adjustment ratio close to 0.5 can be used posteriorly. Additionally, more adjustment ratios can be selected such that the adjustment ratio gradually changes, for example, anteriorly, depending on the anticipated biomechanics of the joint. Changes can also be made to the adjustment ratio as a result of patient specific parameters such as age, sex, weight, ethnicity, and activity level. The adjustment ratio can be selected in order to achieve an optimal biomechanical or functional result. In vitro cadaveric testing, constraint testing, testing of contact surface, fatigue testing and robotic testing can, for example, be used for determining the optimal adjustment ratio(s) for an implant.

Finally, to determine the shape of the superior surface of the implant, the compressed meniscal surface can be combined with the portion of the tibial cartilage surface that is not covered by the meniscus. The shape of, for example, an inferior surface of the implant can be derived from the entire cartilage surface (FIG. 11C) or the subchondral bone surface. The latter can be used, for example, if there is significant eburnation of the joint and most of the cartilage has been lost.

XI. Derivation of Superior Implant Surface in Case of Damaged Meniscus

In patients with a damaged or degenerated meniscus or those that had a prior meniscectomy, the meniscal surface cannot be used as a template for an implant surface as described above. In these cases, a generic meniscal model can be used to design the desired implant surface.

The generic meniscal model can be generated from data that is, for example, collected from cadaveric femoral specimens using a Titanium FaroArm as described above. Alternatively, a laser scanning device or an optical device can be used. In this instance, meniscal surface data can be digitized, for example, from ten frozen cadaveric tibial specimens. All surface data sets obtained can then be matched for size differences using, for example, an affine surface registration scheme. The matched surface points after registration can then be merged into a single point cloud. A generic meniscal surface, $S_g$, can be fitted through a point cloud using a least-squares optimization, resulting in a "mean" surface of the ten specimens.

Typically, dimensions of healthy menisci correlate well with dimensions of bony landmarks. Therefore, measurements of bony landmarks in an MRI can be used to reconstruct the dimensions of the healthy meniscus (see, e.g., TABLE 2, above). The antero-posterior length L will be calculated from the length of the femoral condyle. For determining medio-lateral meniscal width W, we can use the position of the medial margin of the tibia for the medial meniscus and the lateral tibial margin for the lateral meniscus. The height H can be derived from the highest point of the tibial spine.

Once the values L, W, and H have been determined, $S_g$ can be deformed accordingly. Each point P in $S_g$ with the coordinates (x, y, z) can be transformed into a new point P' using Equation 4:

$$P'=(x',y',z')=((L/L_g){\cdot}x,(W/W_g){\cdot}y,(H/H_g){\cdot}z) \quad [\text{Eq. 4}]$$

where $L_g$, $W_g$, and $H_g$ are the respective dimensions of $S_g$. The transformed points P' can form the meniscal surface S that will be used as a template for designing the superior implant surface as described in the previous section.

XII. Final Steps of Implant Design

Figure 12:
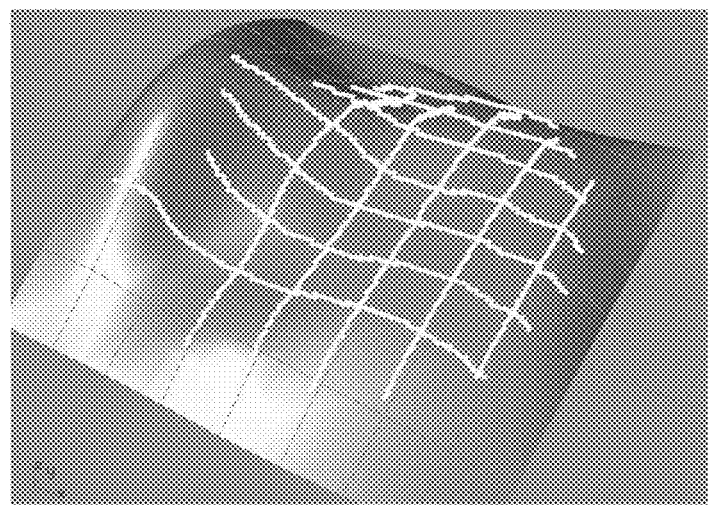
FIG. 12 illustrates a point cloud of an implant surface (yellow) that approximates smooth surface patch (brown).
Figure 15A:
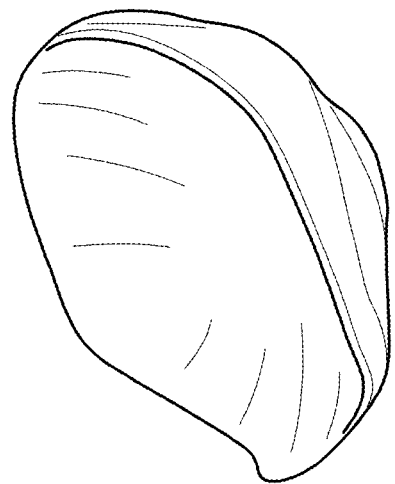
FIGS. 15A-D are views of an implant suitable for the hip.
Figure 15B:
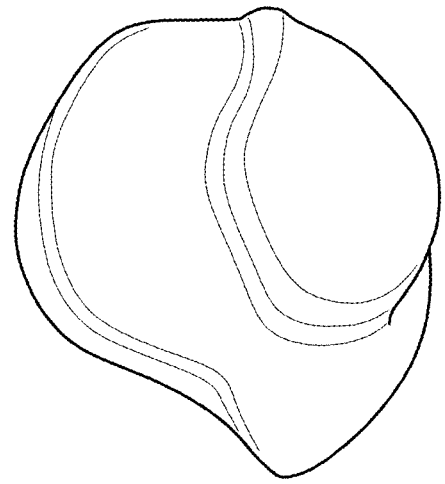
Figure 15C:
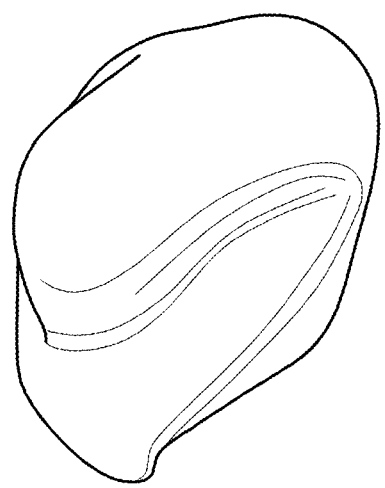
Figure 15D:
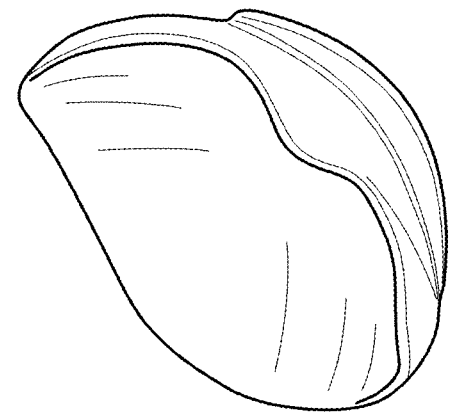

The first and second implant surfaces derived from an MR image, as described above, consist of point clouds. The point clouds can be converted into a data format that then can be manipulated in, for example, a CAD system. The Surface Patch function in the surface modeling program Rhinoceros can be used to approximate a smooth surface patch to the point cloud data (FIG. 12). This surface can then be exported in the IGES format to be read by the CAD software. Other software programs can be used without departing from the scope of the invention. For example, Pro/Engineer, Solid Edge, Alibre and IronCAD are also suitable programs.

Using the CAD software SolidWorks, the superior and inferior surfaces can be combined into one design model. Both surfaces can be clipped using the outer meniscal edge as a margin (FIG. 11).

From this information, joint implants can be designed that take into consideration the dimensions. FIGS. 13A and B are views of a joint implant suitable for use on a condyle of the femur. These views are shown from the inferior and superior surface viewpoints. The surfaces, edges and height of the implant can be adjusted to account for the measurements taken to achieve an implant with an optimal patient fit. FIG. 14 is a view of an implant suitable for placement in a joint knee and placed on a portion of the tibial plateau. FIGS. 15A-D are views of an implant suitable for the hip. These implants can also be designed so that the surfaces, edges and height of the implants can be adjusted to account for the measurements taken as well as the patient specific criteria, as appropriate or desirable.

XIII. Accuracy of 3D Imaging and 3D Sizing Techniques for Deriving 3D Shape of Implant In order to determine how much the predicted meniscal surface, calculated from the generic model, differs from the true shape of the meniscus, healthy volunteers can be examined. Suitable spiral CT, also with intravenous or intra-articular contrast enhancement, or MRI images can be acquired, from which medial and lateral menisci can then be extracted using live wire segmentation, or other suitable mechanisms. Furthermore, the generic models for the medial and lateral meniscus can be fitted as described above. For each subject, the medial and lateral meniscus that was segmented from the MRI can be compared to the fitted models as follows:

1. For each point $P=(x,y,z)$ in the segmented data set choose the closest point $P_1=(x_1,y_1,z_1)$ from the fitted model with $z_1 \geq z$ and the two closest points $P_2=(x_2,y_2,z_2)$ and $P_3=(x_3,y_3,z_3)$ with $Z_2, Z_3 \leq Z$.
2. The point P is projected orthogonally onto the plane defined by $P_1$, $P_2$ and $P_3$. The projected point P' is given by:

$$P'=P-((P-P_1,n)/(n,n))$$

where n is the normal to the plane and (•,•) denotes the dot product.

3. Calculate the distance $d_1$ between P and the plane, given by $$d_1=\|P'-P\|.$$

4. Repeat 1-3 with $P_1=(x_1,x_1,z_1)$ such that $z_1 \leq z$ and $P_2=(x_2,y_2,z_2)$ and $P_3=(x_3,y_3,z_3)$ such that $z_2, z_3 \geq z$, resulting in $d_2$.
5. Calculate the mean distance for P: $d(P)=(d_1+d_2)/2$.
6. Calculate the total distance measure D over all points in the segmented data set:

$$D=\Sigma_p d(P).$$

The total distance measure D depends on the relative position of the segmented MRI data and the fitted model in the coordinate system. This relative position can be optimized to minimize D by adjusting the rigid body transformation T that positions the model in an iterative registration process based on the iterative closest point algorithm, using D(7) as a cost function.

Typically, it is anticipated that the accuracy of this fitting approach is sufficient if the average distance D/n, where n is the number of points in the segmented data, is below 1.5 mm.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims and equivalents.

What is claimed is:

1. A method for designing a system for repairing a joint of a patient comprising:
   acquiring at least one of an isotropic data volume or near isotropic data volume from electronic image data the joint of the patient;
   deriving from the isotropic or near isotropic data volume measurements of at least one articular surface of the joint, wherein the measurements include at least one patient-specific dimension or shape parameter; and
   designing a patient-specific portion of a component of the system using the at least one patient-specific dimension or shape parameter.

2. The method of claim 1, wherein the electronic image data includes isotropic or near-isotropic three-dimensional image data.

3. The method of claim 1, wherein the electronic image data includes image data obtained from scans in at least two planes that intersect.

4. The method of claim 1, wherein the articular surface of the joint includes a subchondral bone surface of the joint.

5. The method of claim 1, wherein the articular surface of the joint includes a cartilage surface of the joint.

6. The method of claim 5, wherein the cartilage surface includes a diseased or damaged cartilage surface of the joint.

7. The method of claim 1, wherein the joint is a knee joint and the system includes a tibial implant for repairing the knee joint.

8. The method of claim 7, wherein the patient-specific dimension or shape parameter includes a measurement of a tibial plateau of the knee joint.

9. The method of claim 7, wherein the patient-specific dimension or shape parameter includes a measurement of a tibial spine of the knee joint.

10. The method of claim 7, wherein the patient-specific dimension or shape parameter is selected from the group consisting of: a tibial bone dimension, a tibial cartilage measurement including thickness and/or shape, a femoral condyle bone dimension, a femoral cartilage measurement including thickness and/or shape, a patellar bone dimension, a patellar cartilage dimension including thickness and/or shape, a measurement of a ligament of the knee joint, and any combination thereof.

11. The method of claim 10, wherein the tibial bone dimension is selected from the group consisting of a maximum anterior-posterior distance, a maximum medial-lateral distance, a maximum distance from the tibial spine to the edge, a width of a tibial spine, a height of a tibial spines, an area of tibial plateau occupied a tibial spine, a depth of a tibial plateau, a 2D shape of a tibial plateau, a 3D shape of a tibial plateau, and any combination thereof.

12. The method of claim 10, wherein the femoral bone dimension is selected from the group consisting of a maximum anterior-posterior distance, a maximum superior-inferior distance, a maximum medial-lateral distance, a maximum distance from a trochlea to the medial or lateral edge; a width of an intercondylar notch, a depth of an intercondylar notch, a curvature at a select region along one or both femoral condyles, a 2D of a femoral condyle, a 3D shape of a femoral condyle, and any combination thereof.

13. The method of claim 10, wherein the measurement of the ligament of the knee joint includes a size, length, or shape of the ligament.

14. The method of claim 1, wherein the joint is a knee joint and the system includes a femoral implant for repairing the knee joint.

15. The method of claim 14, wherein the patient-specific dimension or shape parameter includes a medio-lateral width of a lateral femoral condyle of the knee joint.

16. The method of claim 14, wherein the patient-specific dimension or shape parameter includes a medio-lateral width of a medial femoral condyle of the knee joint.

17. The method of claim 1, wherein the joint is a hip joint, a shoulder joint or an ankle joint of the patient.

18. A method for selecting a system for repairing a joint of a patient comprising:
- acquiring at least one of an isotropic data volume or near isotropic data volume from electronic image data the joint of the patient;
- deriving from the isotropic or near isotropic data volume measurements of at least one articular surface of the joint, wherein the measurements include at least one patient-specific dimension or shape parameter; and
- selecting a component from pre-made components having a corresponding portion that closely matches the at least one patient-specific dimension or shape parameter.

19. The method of claim 18, wherein the step of selecting includes selecting a computer-readable model of the selected component from pre-made components.

* * * * *